United States Patent [19]

Hercend et al.

[11] Patent Number: 6,114,516

[45] Date of Patent: Sep. 5, 2000

[54] NUCLEOTIDE SEQUENCES CODING FOR VARIABLE REGIONS OF THE αCHAINS OF HUMAN T LYMPHOCYTE RECEPTORS, CORRESPONDING PEPTIDE SEGMENTS AND THE DIAGNOSTIC AND THERAPEUTIC MUSES

[75] Inventors: Thierry Hercend, Nogent-sur Marne; Frederic Triebel, Seine; Sergio Roman-Roman; Laurent Ferradini, both of Paris, all of France

[73] Assignee: Hoechst Marion Roussel, France

[21] Appl. No.: 09/041,090

[22] Filed: Mar. 12, 1998

Related U.S. Application Data

[62] Division of application No. 08/348,572, Apr. 19, 1995, Pat. No. 5,817,511, which is a continuation of application No. 07/934,529, Nov. 24, 1992, abandoned.

[30] Foreign Application Priority Data

Feb. 8, 1991 [FR] France .................................. 91 01487
Apr. 12, 1991 [FR] France .................................. 91 04527

[51] Int. Cl.[7] ........................... C12N 15/11; C12N 15/63; C07K 5/00; C07K 14/00

[52] U.S. Cl. ..................... 536/23.5; 435/320.1; 530/324; 530/350

[58] Field of Search ........................ 536/23.5; 435/320.1; 530/350, 324

[56] References Cited

U.S. PATENT DOCUMENTS 5,817,511 10/1998 Hercend et al. .

OTHER PUBLICATIONS

Russo, G., et al. Proc. Natl. Acad. Sci. U.S.A. 86:602–606, Jan. 1989.
Baer, R., et al. EMBO J. 7:1661–1668, 1988.
Yoshikai, Y., et al. J. Exp. Med. 164:90–103, Jul. 1986.
Loh, E.Y., et al. Science. 243:217–220, Jan. 13, 1989.

*Primary Examiner*—Christina Y. Chan
*Assistant Examiner*—Ronald Pelley
*Attorney, Agent, or Firm*—Bierman, Muserlian and Lucas

[57] ABSTRACT

The present invention relates to new nucleotide sequences coding for variable regions of the α chains of human T lymphocyte receptors, corresponding peptide segments and the diagnostic and therapeutic uses.

4 Claims, 5 Drawing Sheets

Vα 1

```
                    1
IGRa08    AGTGTTTCCCTTGCTCAGCCATGTCCTTATCCCACTGCTGGGAGCTTATACATTTGTCCTGAGAACTGCCAGAGCCCAGTCAGTGACCCAGCCTGA
IGRa08    CATCCACATCACTGTCTCTGAAGGAGCCTCACTGGAGTTGAGATGTAACTATTCCTATGGGCAACACCTTATCTCTTCTGGTATGTCCAGTCCCCGGC·
IGRa08    CAAGGCCTCCAGCTGCTCCTGAAGTACTTTCAGGAGACACTCTGGTTCAAGGCATTAAAAGGCTTTGAGGCTGAATTTAAGAGGAGTCAATCTTCCTTCA
IGRa08/   ACCTGAGGAAACCCTCTGTGCATTGGAGTGATGCTGCTGAGTACTTCTGTGCT      333
AE11                                                            102
IGRa08/   .T.............
AE11
```

```
          AAATCCTTGAGAGTTTTACTAGTGATCCTGTGGCTTCAGCTGAGCCGGGTTTGGAGCCAACAGAAGGAGGTGGAGCA
IGRa09    GAATTCTGGACCCCTCAGTGTTCCAGAGGGAGCCATTGCCTCTCCAACTGCTCTCACTGCCTGAGGTTCCCAGTCAGTGACCGAGGTTCCTCTTCTGGTACAGACAATAT
IGRa09/   TCTGGGAAAAGCCCTGAGTTGATAATGTCCATATACTCCAATGGTGACAAAGAAGATGGAAGGTTTACAGCACAGTCAATAAAGCCAGCCAGTATGTTT
AF110
IGRa09/   CTCTGCTCATCAGAGACTCCCAGCCCAGTGATTCAGCCACCTACCTCTGTGCC     330
AF110                                                            252
```

```
IGRa10    GGCCACACATTTGGGGAGACGAAATGGAGTCATCCCTGGGGAGGTGTTTGCTGATTTGTGGCTTCAAGTGGACTGGGTGAAGAGCCAAAAGATAGAACAGAA
                                    1
IGRa10    TTCCGAGGCCCTGAACATTCAGGAGGGTAAAACGGCCACCCTGACCTGCAACTATACAAACTATTCTCCAGCATACTACAGTGGTACCGACAAGATCCA
HAP35     ................................................................................................
IGRa10    GGAAGAGGGCCCTGTTTTCTTGCTACTCATACGTGAAATGAGAAATGAGAAAAGAAAAGAAAAGACTGAAGGTCACCTTTGATACCACCCTTAAACAGAGTT
HAP35     ................................................................................................
IGRa10    TGTTTCATATATCACAGCCTCCCAGCCTGCAGACTCAGCTACTACCCTCTGTGCT    333
HAP35     ......................................................    249
```

```
                                       1
IGRa11    CTCGTGGTATCCTGCAGCAGATGTGGGGAGTTTTCCTTCTTTATGTTTCTTTATGAAGATGGGAGGCACTACAGGACAAAACATTGACCAGCCCACTGAGAT
HAP12     ................................................................................................
IGRa11    GACAGCTACGGAAGGTGCCATTGTCCAGATCAACTGCAGCACGTACCAGCAACATGCTGGGAAGCACCC
HAP12     ................................................................................................
IGRa11    ACATTTCTGTCTTACAATGTTCTGGATGGTTTGGAGGAGAAAGGTCGTTTTCTTCATTCCTTAGTCGGTCTAAAGGGTACAGTTACCTCCTTTTGAAGG
HAP12     ................................................................................................
IGRa11    AGCTCCAGATGAAAGACTCTGCCTCTTACCCTCTGTGCT    318
HAP12     .......................................    222
```

FIG. 1D

Vα22
                1
IGRα12  ATTTGGGTAACACACTAAAGA<u>AT</u>GAACTATTCTCCAGGCTTAGTATCTCTGATACTCTTACTGCTTGGAAGAACCCGTGGAGATTCAGTGACCCAGATGGA

IGRα12  AGGGCCAGTGACTCTCTCAGAAGAGGCCTTCCTGACTATAAACTGCACGTACACAGCCACAGGATACCCTTCCCTTTCTGGTATGTCCAATATCCTGGA

IGRα12
AC9     GAAGGTCTACAGCTCCCTCCTGAAAGCCACGAAGGCTGATGACAAGGGAAGCAACAAAGGTTTTGAAGCCACATACGTAAAGAACCACTTCTTTCCACT

IGRα12                                                                           330
AC9     TGGAGAAAGGCTCAGTTCAAGTGTCAGACTCAGCGGTGTACTTCTGTGCT ......                  113

FIG. 1E

F   G   G   T
IGRJα01G <u>GGTTATTGCAATAGCACTAAAGACTGTGTAACACCAATGCAGGCAAATCAACCTTTGGGGATGGGACTACGCTCACTGTGAAGCCA</u>
IGRJα02G <u>GGTTTTTGTAAAGAATGAGCCCATTGT</u>GGATAGGCTTTGGGAATGTGCTGCATTGCGGGGTCCGGCACTCAAGTGATTGTTTTACCA

IGRJα04                                             TAGATACTGGAGGCTTCAAAACTGTCTTTTGGAGCAGGAACAAGAGACTATTTGTTAAAGCA
IGRJα05                                               CCTAACTGGGGAAGCCAAGGAAATCCATCTTTGGGACTGAAGCGAGACTTCACCGTTCTTCCC
IGRJα06                                                 ATGGAGGAAGCCAAGGAAATCCATCTTTGGAAAAGGCACTCACTCTCTGTTAAACCA
IGRJα07                                                   GGAGCCAATAGTAAGCTGACATTTTGGAAAGGAGCAGGGACTAGACCA
IGRJα08                                                      CTGGTGGCTACAATAAGCTGATTTTTGGAGCAGGGAACCAGGCTGCTGTACACCCA
IGRJα09                                                          TGGAAAACAAGCTGGTCTTTGGCGCAGGAACCATTCTGAGAGTCAAGTCC

FIG. 2

NUCLEOTIDE SEQUENCES CODING FOR VARIABLE REGIONS OF THE αCHAINS OF HUMAN T LYMPHOCYTE RECEPTORS, CORRESPONDING PEPTIDE SEGMENTS AND THE DIAGNOSTIC AND THERAPEUTIC MUSES

PRIOR APPLICATION

This application is a division of U.S. patent application Ser. No. 348,572 filed Apr. 19, 1995, now U.S. Pat. No. 5,817,511 which is a continuation of U.S. patent application Ser. No. 934,529 filed Nov. 24, 1992, now abandoned.

The present invention relates to new nucleotide sequences coding for variable regions of α chain T-cell receptors, corresponding peptide segments and the diagnostic and therapeutic uses.

It is known that the receptors recognizing antigens at the surface of mature T lymphocytes (hereafter designated T-cell receptors) possess a structure having a certain similarity with those of immunoglobulins. Therefore, they contain heterodimeric structures containing α and β glycoprotein chains or γ and δ glycoprotein chains (see Meuer et al. (1), Moingeon et al. (2), Brenner et al. (3), Bank et al. (4)).

The directory of T-cell receptors must be able to address the immense diversity of antigenic determinants. This is obtained by genetic recombination of different discontinuous segments of genes which code for the different structural regions of T-cell receptors. Thus, the genes contain V segments (variable segments), optionally D segments (diversity segments), J segments (junction segments) and C segments (constant segments). During the differentiation of T-cells, specific genes are created by recombination of V, D and J segments for the β and δ loci and V and J segments for the α and γ loci. These specific combinations as well as the pairing of two chains create the combinational diversity. This diversity is highly amplified by two supplementary mechanisms, namely the imprecise recombination of V-D-J or V-J segments and the addition of nucleotides corresponding to the N region (Davis et al. (5)).

A certain number of genetic V segments are already known. These segments have been grouped into subfamilies as a function of the similarity of sequences. By definition, the segments which have more than 75% similarity in the nucleotide sequence have been considered as members of the same subfamily (Crews et al. (6)). The known Vα genetic segments have also been classified into 22 subfamilies, 14 of which have only one member (see Concannon et al. (7), Kimura et al. (8), Wilson et al. (9)).

Moreover, about 60 J genetic segments have been described (9).

Furthermore, monoclonal antibodies directed against specific segments of the variable parts of T-cell receptors, in particular the β or δ chains, were recently described in WO 90/06758. These monoclonal antibodies are useful not only as diagnostic tools but also as therapeutic tools, for example, vis-à-vis rheumatoid athritis.

The use of synthetic peptides corresponding to the variable regions of the α or β chains in the treatment of auto-immune diseases is also described (23 and 24).

It is also known that variations exist from one individual to another in the expression of different variable segments of the T-cell receptor in man (27 and 28).

The present inventions aims to enrich the directory of genetic segments coding for the variable regions of the chains of T-cell receptors by providing on the one hand new Vα genetic segments belonging to new subfamilies or belonging to subfamilies of which at least one member is already known, and on the other hand, new Jα genetic segments.

Therefore a subject of the present invention is nucleotide sequences coding for the variable regions of α chains of human T lymphocyte receptors, corresponding to cDNA's containing nucleotide sequences chosen from any one of the following:

a—Vα segments corresponding to one of the sequences SEQ ID No. 1 to 11, and b—Jα segments corresponding to one of the sequences SEQ ID No. 12, 13 and 15 to 20, and the sequences which differ from them by one or more nucleotides.

More particularly a subject of the present invention is:

sequences coding for the variable regions of α chains of human T lymphocyte receptors, corresponding to cDNAs containing nucleotide sequences chosen from any one of the Vα segments corresponding to one of the sequences SEQ ID No. 1 to 10 and the sequences which differ from them by one or more nucleotides, sequences coding for the variable regions of α chains of human T lymphocyte receptors, corresponding to cDNAs containing nucleotide sequences chosen from any one of the Jα segments corresponding to one of the sequences SEQ ID No. 12, 13 and 15 to 20 and the sequences which differ from them by one or more nucleotides.

The expression "and sequences which differ from them by one or more nucleotides", encompasses alleles which differ by up to 8 nucleotides, but more often differ by 1 or 2 nucleotides or which can differ by the deletion or addition of one or two codons.

Also a more particular subject of the invention is:

nucleotide sequences coding for the variable regions of α chains of human T lymphocyte receptors, corresponding to cDNAs corresponding to all or part of the nucleotide sequences chosen from any one of the Vα segments corresponding to one of the sequences SEQ ID No. 2 to 5, and the sequences which differ from them by one or two nucleotides, nucleotide sequences coding for the variable regions of the α chains of human T lymphocyte receptors, corresponding to cDNAs corresponding to all or part of the nucleotide sequences chosen from any one of the Vα segments corresponding to one of the sequences 1 to 200 of SEQ ID No. 1

1 to 467 of SEQ ID No. 6

1 to 77 of SEQ ID No. 7

1 to 151 of SEQ ID No. 8

291 to 386 of SEQ ID No. 9

1 to 260 of SEQ ID No. 10 and the sequences which differ from them by one or two nucleotides, nucleotide sequences coding for the variable regions of the α chains of human T lymphocyte receptors, corresponding to cDNAs corresponding to all or part of the nucleotide sequence corresponding to SEQ ID No. 11 and which contain the 108 nucleotide, nucleotide sequences coding for the variable regions of the α chains of human T lymphocyte receptors, corresponding to cDNAs corresponding to all or part of the nucleotide sequences chosen from any one of the Jα segments corresponding to one of the sequences SEQ ID No. 12, 13 and 15 to 20 and the sequences which differ from them by one or two nucleotides.

By the expression "nucleotide sequences corresponding to cDNAs corresponding to all or part of the nucleotide sequences" is also designated the complete sequences as well as fragments of these sequences including short fragments (oligonucleotides) which can be used as probes (generally containing at least 10 nucleotides) or as primers (generally containing at least 15 nucleotides). In a general fashion, the invention encompasses the group of new oligonucleotides which are fragments of Vα and Jα sequences according to the invention.

As to the sequences which differ by one or two nucleotides, they correspond to variations which are observed experimentally at the time of determination of the nucleotide sequence of several cDNAs.

Also a subject of the present invention is the peptides coded by the nucleotide sequences according to the invention as well as the alleles and the derivatives of the latter which have the same function.

Also a subject of the present invention is the peptides constituted by or composed of a peptide sequence coded by all or part of the sequence 108 to 364 of SEQ ID No. 11.

In a general fashion, the present invention encompasses the peptides constituted by or composed of a peptide sequence coded by the nucleotide sequences according to the invention as well as fragments of these peptides. It also encompasses the peptides which differ from the latter by one or more amino acids and which have the same function. These peptides can correspond to modifications such as those known with muteins or to allelic variations. In fact it has been shown in particular that certain genetic segments coding for the variable regions of chains of T receptors in man were subjected to a phenomenon of genetic polymorphism called allelic variation (25). The present invention encompasses the peptides resulting from this phenomenon.

The nucleotide sequences according to the invention have been obtained according to the following stages:

isolation of the RNA's of peripheral lymphocytes of an individual;

obtaining the complementary DNA using reverse transcriptase and a primer A which is specific to the Cα region (SEQ ID No. 21);

genetic amplification (by Anchored Polymerase Chain Reaction or A-PCR) using a DNA polymerase, a poly C primer (SEQ ID No. 22) and a primer B which is specific to the Cα region (SEQ ID No. 23);

a new amplification by A-PCR using DNA polymerase and a primer C which is specific to the Cα region (SEQ ID No. 24);

insertion in a plasmid vector;

transformation of a bacterial host with the recombinant vector;

screening of recombinant bacterial colonies with a labelled oligonucleotide D which is specific to Cα (SEQ ID No. 25);

extraction of plasmids from positive colonies;

and sequencing of DNA fragments containing the Cα region.

The present invention can be reproduced, in particular, by bispecific genetic amplification (polymerase chain reaction or PCR) by starting with the peripheral lymphocytes which express the mRNA including the variable or junctional segments corresponding to sequences ID No. 1 to 13 and 15 to 20 of the invention or alternatively by applying this PCR technique to genomic DNA of any somatic cell of an individual taken at random. The invention can also be reproduced by preparing the above genetic sequences by the chemical synthesis of oligonucleotides.

The peptides according to the invention can be obtained by standard peptide synthesis. They can also be obtained by the application of known genetic engineering techniques including the insertion of a DNA sequence coding for a peptide according to the invention into an expression vector such as a plasmid and the transformation of cells with this expression vector.

Therefore a subject of the present invention is also plasmids and expression vectors containing a DNA sequence coding for a peptide according to the invention as well as the hosts transformed with this vector.

Also a subject of the present invention is antibodies, and, in particular, monoclonal antibodies directed, against an antigenic determinant belonging to or composed of a peptide according to the invention.

The monoclonal antibodies may be obtained by any of the techniques which allow the production of antibody molecules from cell line culture. These techniques include different techniques using hybridomas.

The antibody production may be obtained in animals by the immunization of the animals by injection with the peptides or fragments according to the invention, whether they be natural, recombinant or synthetic, optionally after coupling to an immunogen such as tetanic anatoxin, or also by injection of human T lymphocytes expressing the corresponding sequences at their surface, including recombinant cells transfected with the corresponding coding sequences.

Also a subject of the present invention is hybridomas producing monoclonal antibodies directed against the polypeptides according to the invention.

The present invention also encompasses the fragments and the derivatives of monoclonal antibodies according to the invention which are reactive with defined variable regions of T-cell receptors. These fragments are, in particular, the F(ab')$_2$ fragments which can be obtained by the enzymatic cleavage of antibody molecules with pepsin, the Fab' fragments which can be obtained by reduction of the disulphide bridges of F(ab')$_2$ fragments and the Fab fragments which can be obtained by the enzymatic cleavage of antibody molecules with papain in the presence of a reducing agent. These fragments can also be obtained by genetic engineering.

The monoclonal antibody derivatives are for example-antibodies or fragments of these antibodies to which labellers such as a radio-isotope are attached. The monoclonal antibody derivatives are also antibodies or fragments of these antibodies to which therapeutically active molecules are attached, in particular, cytotoxic compounds.

The products of the invention have several uses in the field of diagnostics and in the field of therapeutics.

1—Uses in the field of diagnostics

The oligonucleotides contained in the nucleotide sequences according to the invention can be used to constitute detection probes (generally at least 10 nucleotides) which are capable of hybridizing with a variable region of the α chain or primers for the amplification of DNA (generally containing at least 15 nucleotides and preferably at least 17 nucleotides) which are capable of being linked to a sequence to be amplified.

Thus the oligonucleotides are used in the diagnosis of immune disorders by detecting the presence of nucleic acid sequences which are homologues of a gene coding for the variable regions of α chains of T-cell receptors in the mRNA of a sample from a patient. Different methods can be used to establish a connection between the expression of T-cell genes and an illness. These methods include:

a—the production and analysis of cDNA expression libraries obtained from T-cells connected with the illness to determine the frequency of dominant genes;

b—Southern blot analysis of samples of genomic DNA to determine whether genetic polymorphisms or rearrangements of the genes coding for the T-cell receptors exist;

c—the analysis of samples by obtaining cDNA, amplification by PCR and hybridization with labelled probes;

d—the hybridization in situ of T-cells without culture of T-cells beforehand.

The primers are used in PCR reactions in a method such as that defined in c above.

The monoclonal antibodies, the fragments or the derivatives of these antibodies according to the invention, in particular the anti Vα antibodies, can be used to study T-type immune responses, for example in the field of the auto-immune diseases of oncology, of allergies, of transplants and of infectious diseases. In particular, the directory of different variable α segments of the T receptor can be studied, whether it be blood or tissue T-cells. In a general fashion the techniques used can be in vitro or in vivo methods.

With in vitro methods, the samples used can be samples of body fluids or tissue samples. The techniques used can include in particular flow cytofluorimetry to analyse blood T lymphocytes or labelling with immunoperoxidase on an anatomopathological section to study the lymphocytes infiltrating the tissues.

With in vivo methods, the antibodies, their fragments or their derivatives are administered by the usual routes, for example by intravenous route, and the immunospecific linkages are detected. This can be obtained for example in the case where an antibody is used which is labelled with a radio-isotope.

2—Uses in the therapeutic field

The oligonucleotides contained in the nucleotide sequences according to the invention can be used in therapeutics as anti sense oligonucleotides. In fact it is known that it is possible in vitro to inhibit the expression of a transcript gene in human lymphocytes by incubating these lymphocytes with an anti sense oligonucleotide specific to the gene in question (26). These anti sense oligonucleotides generally contain at least 10 and, preferably, at least 16 nucleotides. These anti sense oligonucleotides can be in particular the inverted and complemented sequences corresponding to 20 nucleotides upstream from the initiation site of the translation (ATG). The significance of the use in vitro of anti sense oligonucleotides specific to a Vα or Jα genetic segment is to abolish (or strongly diminish) the expression of a T receptor containing this Vα or Jα segment and thus to obtain a phenomenon of clonal deletion at the level of the specific reactivity of T lymphocytes. The anti sense oligonucleotides can not only be used in vitro on human T lymphocytes which are then reinjected, but also in vivo by local or systemic injection preferably after modification to increase the stability in vivo and the penetration into the T lymphocytes of these oligonucleotides.

The monoclonal antibodies according to the invention, in particular the anti Vα antibodies can be used to modulate the immune system. It is in this way that the antibodies can be administered to block the interaction of the effector T-cells with their specific antigen. Anti T receptor antibodies linked for example to a cytotoxic molecule or a radio-isotope can also be administered in a way so as to obtain a clonal deletion, thanks to the specific fixation on an α chain of a T-cell receptor. The monoclonal antibodies according to the invention can be used in therapeutics at low mitogenic concentrations so as to activate, in a specific fashion, certain sub-assemblies of T-cells or can be used at much higher concentrations to fix them to the receptors concerned and thus label these sub-assemblies with a view to their elimination by the reticulo-endothelial system. An important criterion in the treatment of an illness is the ability to modulate the sub-assemblies of T-cells linked with an illness. The exact nature of this therapeutic modulation, namely blocking or suppressing a particular sub-assembly of T-cells or on the contrary stimulating and activating a particular sub-assembly, will depend on the illness in question and the specific sub-assembly of T-cells concerned.

This type of treatment has an advantage over current treatments using antibodies such as the treatment with anti CD3 antibodies in patients having had a kidney transplant and having a rejection problem, given that thanks to the invention there will be no modulation of the totality of the T-cell population but only of the sub-assembly of T-cells expressing the α sub-family specific to the T-cell receptors.

Moreover, as the response of T-cells is often oligoclonal, it is generally convenient to use "cocktails" of several antibodies in therapeutics.

In addition anti Vα antibodies can be used to select T lymphocytes in vitro, for example by passing through a column containing spheres carrying the antibody. This separation of certain T lymphocytes can be used with a view to culturing these lymphocytes before reinjection into the patient.

Moreover, all or part of the peptide sequences according to the invention can be used in therapeutics, that is to say the peptide sequences coded by the nucleotide sequences according to the invention or fragments of these sequences (generally containing at least 8 to 10 amino acids). These sequences or these fragments, administered to humans or animals, can act as a decoy, that is to say they fix themselves on the epitope carried by the harmful antigen and stop the reaction of normal T-cells with the antigen, preventing in this way the development of an illness which is aggressive towards the self determinants. They can also be used as immunogens in the manufacture of vaccines (optionally after conjugation with protein carriers).

BRIEF DESCRIPTION OF THE DRAWINGS

The present invention will be described in greater detail hereafter by referring to the annexed figures in which:

FIGS. 1 A to E show in a line both a known V sequence and a partial sequence of an extension according to the invention for the respective sequences SEQ ID No. 6 to 10, marked IGRa 08 to IGRa 12. In these figures, the numbering of nucleotides starts at the ATG initiation codon (which is underlined). The dots indicate identical nucleotides. The sequences which are assumed to be the leader sequences have a line over them.

FIG. 2 shows in a line the new Jα sequences (SEQ ID No. 12, 13 and 15 to 20) marked IGRJa 01, 02 and 04 to 09. In these sequences the recombination signals of the germinal line are underlined. The amino acids corresponding to highly preserved codons are marked above the sequences. The codons corresponding to a substitution in one position of a preserved amino acid are underlined twice.

Figure 3:
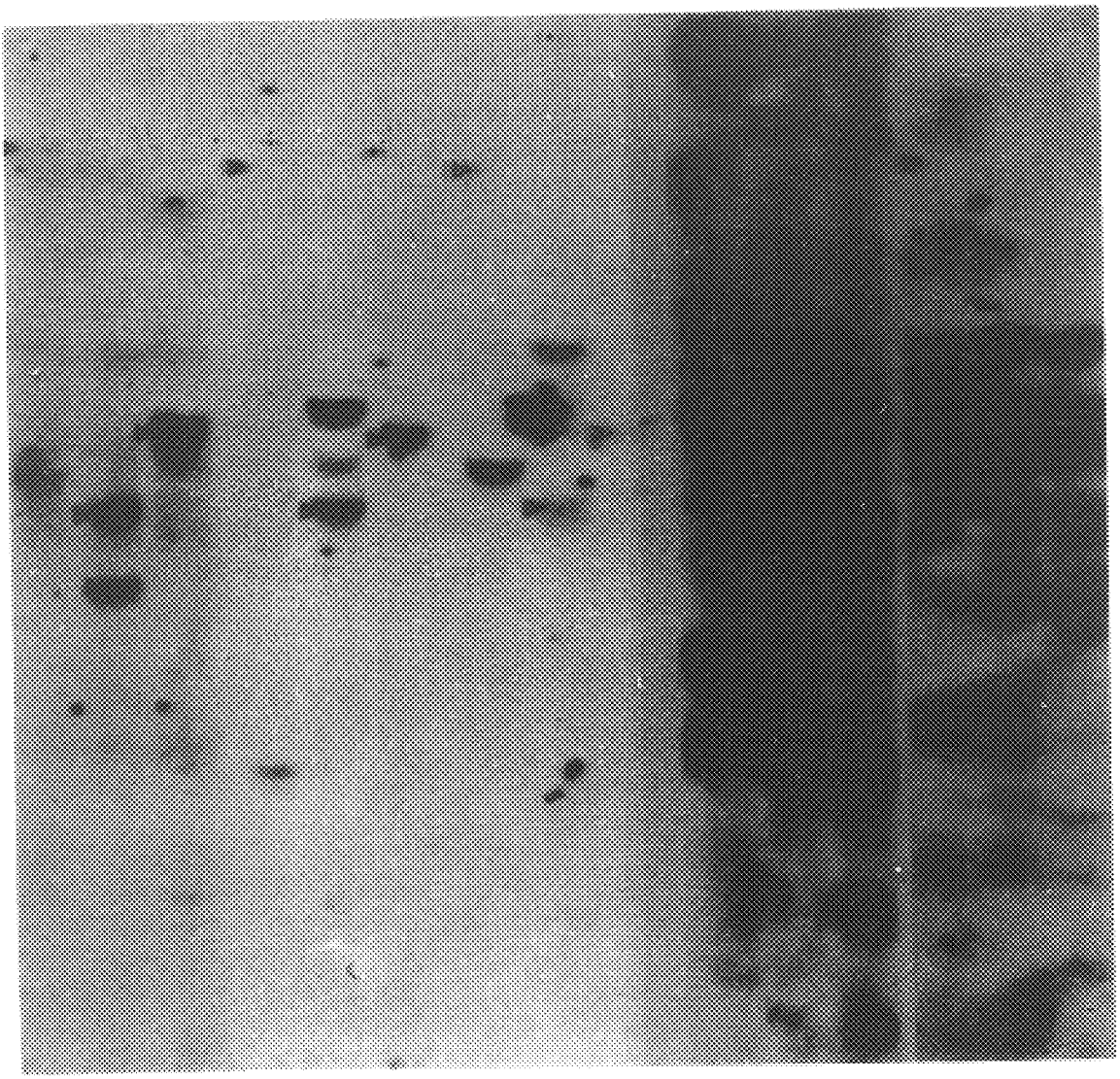
FIG. 3 shows the Southern blot analyses of the genomic DNA treated with a restriction enzyme using probes specific to sequences SEQ ID No. 1 to 5. The restriction enzymes used are EcoRI (column R), Hind III (column H) and Bam III (column B). On this figure the triangles mark the position of DNA fragments hybridizing in a specific fashion with Cα.

I—Obtaining the cDNA and amplification by PCR

The peripheral lymphocytes of an individual are used as the DNA source. The total RNA was prepared according to the method using guanidinium isothiocyanate and caesium chloride (Chirgwin (10)) or according to a one-stage method by extraction with guanidinium isothiocyanate, phenol and chloroform (Chomcyznski (11)).

The first cDNA strand was synthesized in a final volume of 50 microlitres at a temperature of 42° C. for 1 hour using 5 micrograms of total RNA, reverse transcriptase and a primer A which is specific to the Cα region constituted by the sequence 5'-GTTGCTCCAGGCCACAGCACTG (SEQ ID No. 21). This material was then purified by extraction with phenol/chloroform and precipitation with ammonium acetate. After selecting a 0.45/1 kb fraction on agarose gel, the addition of a dG end is carried out on the RNA/cDNA hetero complex in a $CoCl_2$ addition buffer with 14 units of terminal deoxynucleotidyl transferase (TdT) for 30 minutes at 37° C. The reaction was stopped by maintenance at 70° C. for 10 minutes. 1 N NaOH (⅓ volume) was added and the sample was incubated at 50° C. for 1 hour to hydrolyze the RNA, then neutralized with Tris HCl 2 M pH 8 and 1 N HCl. After extraction with a phenol/chloroform mixture the first cDNA strand at end G was precipitated with ethanol and subjected to an amplification using the PCR technique (Polymerase Chain Reaction described by Saiki et al. (12)) in a final volume of 100 microlitres containing 50 mM of KCl, 10 mM of Tris-Cl pH 8.3, 1.5 mM of $MgCl_2$, 0.1% (weight/volume) of gelatine, 200 micromoles of dNTP, 2.5 units of Taq polymerase and 100 picomoles of two primers. The two primers used are, on the one hand a poly-C primer (5'-GCATGCGCGCGGCCGCGGAGG-14C) (SEQ ID No.22) described by Loh et al. (13) as well as a primer B specific to the Cα region (5'-GTCCATAGACCTCATGTCCAGCACAG) (SEQ ID No. 23).

25 amplification cycles are carried out followed by a final 15 minute elongation period at 72° C. Each cycle includes a denaturation stage at 92° C. for 1 minute, a hybridization stage at 55° C. for 2 minutes and an elongation period at 72° C. for 4 minutes. The amplified products are then precipitated with ethanol, resuspended in 30 mM of sodium acetate pH 5, 50 mM NaCl, 1 mM $ZnCl_2$, glycerol 5% by volume and ¹⁄₁₀ of this material is purified as a function of size on a 1% low melting point agarose gel.

A second amplification phase is then carried out directly on approximately 10% of the band containing the agarose following the same conditions as previously, except that the primer 5'-ATACACATCAGAATTCTTACTTTG (SEQ ID No. 24) is used as primer C which is specific to the Cα region. The reaction mixture is then precipitated with ethanol and resuspended in 60 $\mu$l of $H_2O$.

II—Cloning and sequencing of cDNA's

⅓ of the product of the second amplification is digested with Sac II, separated on 1% agarose gel and purified by absorption on glass beads. The material is inserted in the Bluescript SK⁺ vector (Stratagene, La Jolla, U.S.A.) and the recombinants obtained are used to transform the XL1-blue strains of E. Coli (Stratagene). After sedimentation in the presence of X-gal and IPTG, a test is carried out on the white colonies using a "dot blot" technique and a third oligonucleotide specific to the Cα region (5'-GTCACTGGATTTAGAGTCT) (SEQ ID No. 25) labelled with $^{32}p$ is used as a probe. The plasmid DNA of positive colonies is extracted and sequencing takes place under the two strands by the process of termination of the dideoxy chain (Sanger et al. (14)) with Sequenase 2.0 (United States Biochemicals, Cleveland, U.S.A.) following the supplier's recommendations. With the exception of the Sequence SEQ ID No. 5, all the nucleotide sequences were determined on the two strands using at least two distinct clones of cDNA.

The sequences obtained were compared with published Vα and Jα sequences using the method developed by Lipman and Pearson (15). The presumed start codons were identified by searching for the presence of the Kozak consensus sequence for the initiation sites of translations in the eukaryotic cells (Kozak (16)). The presence of hydrophobic leader sequences of the N-terminal side was detected by analysis of the hydrophobicity according to the method described by Kyte (17).

III—Southern blot analysis

The DNA was extracted from the human erythroleucemic cell line K562 and digested with one of the following restriction enzymes: EcoR I, BamH I or Hind III. The DNA (15 micrograms) was subjected to electrophoresis on 0.7% agarose and transferred onto Nylon membranes as described by Triebel et al. (18). The hybridizations were carried out at 65° C. with 6xSSC, 0.5% of SDS, 5xDenhardt's and 100 micrograms of denatured salmon sperm DNA for 16 hours. The membranes were washed at 65° C. with 2xSSC, 0.2% of SDS.

As Vα specific probes, are used the probes obtained by amplification of V-J-C cDNA (>500 bp) containing Vα fragments corresponding to sequences SEQ ID No. 1 to 5 using as a primer the poly-C primer and the C primer. The probes were purified on 1% agarose gel. DNA probes labelled with $^{32}p$ were prepared from fragments purified on agarose by the Feinberg method (19).

IV—Results

By using the A-PCR method, 308 cDNA which hybridize with the Cα clone were cloned, then sequenced. Among these, 172 cDNA correspond to the V-J-C α variable regions only.

The Vα and Jα sequences of the invention are shown in the list of sequences under SEQ ID No. 1 to 11 and SEQ ID No. 12, 13 and 15 to 20 respectively. The sequences SEQ ID No. 2 to 5 correspond to the new sub-families (designated Vα 25, Vα 26, Vα 27 and Vα 29 respectively) while the sequences SEQ ID No. 1 and 6 to 11 correspond to extensions of known V segments.

1. Vα sequences corresponding to new sub-families

The Southern blot analyses of germinal line DNA subjected to digestion by endonucleases, using V-J-Cα probes containing Vα fragments corresponding to sequences SEQ ID No. 2 to 5 were carried out in "low stringency" hybridization conditions to identify the number of Vα genetic segments belonging to each family and to characterize the DNA restriction fragments carrying these Vα genetic segments. The representative results are shown in FIG. 3.

These analyses show that the sub-family corresponding to the sequence SEQ ID No. 3 includes at least two genetic segments while the other sequences (SEQ ID No. 2, No. 4 and No. 5) probably correspond to unique members.

The sizes of the germinal DNA restriction fragments are as follows:

SEQ ID No. 2: EcoR I 2.2 kb, Hind III 4.8 and 5.7 kb, BamH I 25 kb

SEQ ID No. 3: EcoR I 4.6 and 7.5 kb, Hind III 4.2 and 6.4 kb, BamH I 23 and 4.5 kb SEQ ID No. 4: EcoR I 7.6 kb, Hind III 18 kb, BamH I 9 and 0.9 kb SEQ ID No. 5: EcoR I 5.9 and 4.8 kb, Hind III 6.6 kb, BamH I 6.5 kb.

2. Sequences corresponding to extensions of known V sequences

SEQ ID No. 1 (IGR a 02) corresponds to an extension of the 5' side of the LINV sequence (171 bp) (mengle-Gaw (20)): This sequence defines the sub-family provisionaly designated Vα w24.

SEQ ID No. 6 (IGR a 08): this sequence corresponds to an extension of the 5' side of the Vα 1 AE11 clone sequence (Klein et al. (21)). The two straight line sequences are represented in FIG. 1A.

SEQ ID No. 7 (IGR a 09): This sequence corresponds to an extension coding for the NH2 terminal end of the Vα 2 AF110 sequence (Klein already quoted). The two straight line sequences are represented in FIG. 1B. The sequence ID No. 7 corresponds to a consensus sequence. The existence of a T instead of a C is observed in position 206.

SEQ ID No. 8 (IGR a 010): This sequence corresponds to an extension of the 5' region of the Vα HAP35 clone (Yoshikai (22)). The two straight line sequences are represented in FIG. 1C. The sequence ID No. 8 corresponds to a consensus sequence. The existence of a G instead of an A in position 307 and the existence of a T instead of a C in position 360 have been observed.

SEQ ID No. 9 (IGR a 11): This sequence corresponds to an extension of the 3' side of the Vα 7 HAP12 sequence (Yoshikai already quoted). The straight line of the sequences is represented in FIG. 1D. The sequence ID No. 9 corresponds to a consensus sequence. The existence of a C instead of a T in position 86 has been observed.

SEQ ID No. 10 (IGR a 12): This sequence includes the complete coding region of a gene of the Vα 22 sub-family which had been previously identified by the partial sequence (113 bp) AC9 (Klein already quoted). The two straight line sequences are represented in FIG. 1E.

SEQ ID No. 11 (IGR a 13): This sequence corresponds in part to the HAVT 32 and HAVT 35 clones (belonging to the Vα 16 (8) sub-family and which have been described as pseudogenes. In fact, following the addition of a nucleotide in position 108, the SEQ ID No. 11 codes for an original variable region of a T lymphocyte receptor. Moreover, this sequence is equivalent to a sequence HSTCAYM (Klein et al. (21)) for the coding part. However, the sequence SEQ No. 11 is the only one which is complete and coding.

3. Jα sequences

The set of new Jα sequences are represented in FIG. 2. Among the 8 Jα segments, the majority of them have a highly preserved amino acid sequence FGXGT of Jα segments as described by Yoshikai already quoted. However, for the IGRJa 07 segment the threonine residue is replaced by an isoleucine residue.

In addition, instead of a phenylalanine residue a cysteine residue is found in IGRJa 02G.

The present invention also aims at providing specific oligonucleotides of different Vα sub-families, which can be used as primers for the amplification of DNA corresponding to these different Vα sub-families, with a view, for example, of a study of the expression of certain Vα sub-families in a patient and finally of a diagnosis of immune disorders, as indicated above.

The predominant expression of certain Vα sub-families has already been studied using an incomplete range of oligonucleotides. In this way Nitta et al. (29) have described the predominant expression of Vα 7 genes in the lymphocytes infiltrating the tumours. Moreover, Sottini et al. (30) have described the study of the directory of Vα 's, in patients suffering from rheumatoid arthritis.

The present invention aims to provide a complete range of oligonucleotides allowing the study, of both known Vα sub-families and new Vα sub-families of the invention and which are completely specific to each sub-family. Thus the oligonucleotides have been chosen and synthesized to this end and to the requirements of modifications of one or two nucleotides which have been introduced relative to the natural sequences to reduce the cross-reactions between sub-families.

Thus a subject of the present invention is also oligonucleotides which can be used as primers for the amplification of DNA corresponding to the variable regions of α chains of T-cell receptors, chosen from the sequences SEQ ID. No. 26 to 54.

Also a subject of the present invention is the use, as primers for the amplification of DNA corresponding to the variable regions of α chains of T-cell receptors, of oligonucleotides chosen from the sequences SEQ ID No. 26 to 54.

Also a subject of the present invention is a detection process of nucleotide sequences coding for the Vα segments of T receptors or of cDNA-corresponding to transcription products of the latter, in a biological sample, characterized in that it includes:

a) the amplification of DNA with at least one pair of primers formed by one of the oligonucleotides chosen from the sequences SEQ ID No. 26 to. 54 and one oligonucleotide belonging to segment Cα, and b) the detection of amplified sequences with a Cα probe.

The oligonucleotide belonging to a Cα segment used for the amplification can be, in particular, chosen from the sequences SEQ ID No. 55 and 56.

To check the efficiency of the amplification, the operation is preferably carried out in the presence of a pair of control primers and the corresponding control sequence amplified using a corresponding control probe is detected.

This pair of control primers can correspond to two Cβ segments, for example the CβF and CβK primers corresponding to sequences SEQ ID No. 61 and 62. Then a Cβ detection probe is used (corresponding for example to the sequence SEQ ID No. 63). But this pair of primers can also be constituted by two primers belonging to β-actin, notably those corresponding to sequences SEQ ID No. 58 and 59. Then a detection probe corresponding to a sequence of β-actin, such as the sequence SEQ ID No. 60, is used.

Also a subject of the present invention is a diagnostic kit for the implementation of the process defined previously, which includes:

a) at least one oligonucleotide chosen from the sequences SEQ ID No. 26 to 54, b) a Cα primer, c) a Cα probe.

In addition such a kit advantageously contains:

d) a pair of control primers, e) a control probe.

This kit can contain in particular:

a) the group of 29 oligonucleotides corresponding to sequences SEQ ID No. 26 to 54, b) a Cα primer chosen from the sequences corresponding to sequences SEQ ID No. 55 and 56, c) a pair of control primers for β-actin having a sequence corresponding to sequences SEQ. ID NO. 58 and 59 respectively, d) a Cα probe corresponding to the sequence SEQ ID No. 57, e) a control probe for β-actin corresponding to the sequence SEQ ID No. 60.

In the information given in the list of sequences for the sequences 26 to 60, the sequences SEQ ID No. 26 to 47 correspond to sequences belonging to clones of known Vα 1 to Vα 22 sub-families (available from the EMBL database) or to sequences which differ from them by one or two nucleotides.

The sequences SEQ ID No. 49, 50, 51, 52 and 54 correspond to sequences belonging to clones of new sub-families of the invention, corresponding to sub-families provisionally designated vα w24, Vα w25, Vα w26, Vα w27 and Vα w29 (w indicating that the designation is pending definitive designation).

The sequences SEQ ID No. 48 and 53 correspond to sequences belonging to clones IGRa01 and IGRa06 respectively of known sub-families but having not yet received definitive designation (Vα w23 and, vα w28 respectively) one member element of which has already been described (Hinkkanen A. et all (31) and Bernard O. et al. (32) resplectively). The complete sequence of IGRa06 has not yet been published.

The sequences SEQ ID No. 55 and 56 are two examples of oligonucleotides which can be used as Cα primers for amplification.

The sequence SEQ ID No. 57 is the sequence of a C probe which can be used for the detection of amplified DNAs.

The sequences SEQ ID No. 58, 59 and 60 are respectively the sequences of a pair of oligonucleotides belonging to the sequence of β-actin which can be used to check the amplification and the sequence of a probe for detecting the corresponding amplified DNAs.

In the list of sequences the position indicated is the position of the 5' end counting from the predicted initiation site of the ATG translation. In the case where the sequences are incomplete (unknown 5' region), the position (marked with an asterisk) is given relative to the first nucleotide of the sequence. The underlined nucleotides correspond to mismatches introduced relative to the natural sequence.

The oligonucleotides were sythesized with an Applied Biosystems 381 A automated DNA synthesize using the β-cyano-ethylphosphoramidite method (Sinha N. et al. (33)) and following the protocol recommended by the manufacturer. The oligonucleotides were detritylated in the apparatus, cleaved from the support and deprotected with ammonia (at 60° C. for 5 hours). The crude products were purified by reverse phase high pressure chromatography on a $\mu$-bondapak C18 column using an acetonitrile gradient (9 to 15%) in a 0.01 M triethylammonium acetate buffer at pH 5.55.

The amplification carried out using the primers according to the invention can be, in particular, the technique of amplification by PCR (Polymerase Chain Reaction) as described by Saiki et al. (12) and in Patents U.S. Pat. Nos. 4,683,195, 4,683,202, 4,889,818.

For the PCR, a double strand DNA can be used which is denatured or a cDNA obtained from RNA using reverse transcriptase as mentioned above.

The polymerization agent is a DNA polymerase, in particular, Tag polymerase.

Generally the amplification cycle is repeated 25 to 40 times.

The probes-which are used for detecting the amplified sequences can be obtained by labelling the oligonucleotides with a radio-active isotope, which leads to detection by autoradiography, or by conjugation with an enzyme such as peroxidase (ECL Amersham system), alkaline phosphatase or β-galactosidase (Tropix Ozyme system), which leads to detection by chemiluminescence.

The following example illustrates the, implementation of the detection process according to the invention The peripheral lymphocytes of a healthy individual were prepared by density gradient centrifugation. The total DNA was extracted according to a one-stage method by extraction with guanidium isothiocyanate, phenol and chloroform (Chomczynski, 11). The complementary DNA was synthesized in a final volume of 20 $\mu$l at 42° C. for one-hour using 1 to 5 $\mu$g of total RNA, the reverse transcriptase and the Cα B primer (1.25 $\mu$M).

The material obtained was then heated at 95° C. for 3 minutes before being subjected to an amplification according to the PCR technique using in parallel each of the specific Vα primers corresponding to sequences SEQ ID No. 26 to 54 and, the Cα B primer specific to the Cα region (SEQ ID No. 56). This amplification was carried out in a final volume of 10 $\mu$l per tube containing 50 mM of KCl, 10 mM of tris-HCl pH 8.3, 1.5 mM of $MgCl_2$, 0.1% (weight/volume) of gelatine, 200 $\mu$M of dNTP, 0.25 units of Taq polymerase and 0.25 M of each primer. A control amplification was carried out in each tube from 25 mN of a DNA fragment of β-actin of 877 base pairs prepared by PCR and Act 1 and Act 2 primers (SEQ ID No. 58 and 59) specific to actin. 30 amplification cycles were carried out followed by a final elongation .stage of 5 minutes at 72° C. Each cycle included a denaturation stage at 94° C. for one minute, a hybridization stage at 65° C. for one minute and an elongation period at 72° C. for one minute.

The products obtained were separated by electrophoresis on 2% agarose gel, transferred onto nylon membranes in an alkaline buffer and hybridized simultaneously with the Cα C oligonucleotide probes (SEQ ID No. 57) and Act 3 (SEQ ID No. 60) labelled with $^{32}p$ by the polynucleotidyl T4 kinase enzyme. The hybridization was carried out at 42° C. for 16 hours in a buffer containing 6×SSC, 0.5% SDS, 5×Denhardt's, 0.05% $NaH_2PO_4$ and 100 $\mu$g/ml of denatured salmon sperm DNA. The membranes were then washed with SSC 6 X, 20 mM $NaH_2PO_4$, twice at ambient temperature for 5 minutes and once at 50° C. for 30 minutes then autoradiographed.

Figure 4:
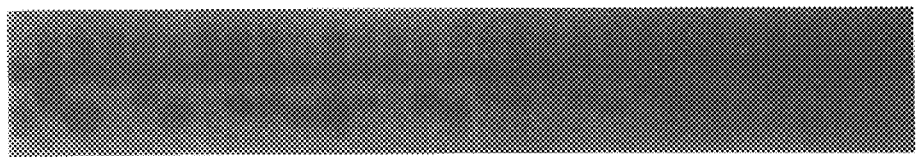
FIG. 4 represents the detection by autoradiography of amplified transcripts of TCR α chains expressed by the peripheral lymphocytes of a healthy individual and of a co-amplified β-actin control.

The results obtained are shown in FIG. 4.

The actin control (band of 877 base pairs) allows the amplification to be verified in all wells. A specific signal appears below this band the size of which corresponds to the size of corresponding amplified fragments, each fragment having a length corresponding to the distance between the locus of the specific Vα oligonucleotide and the Cα primer.

With the individual tested, FIG. 4 shows the preferential expression of certain genetic segments defined relative to the others. For example, the vα 27, 28 and 29 sub-families are less well represented than the Vα 2, 3 and 6 sub-families.

REFERENCES

1. Meuer, S . C., et al., J. Exp. Med. 1983. 157:705.
2. Moingeon, P, et al., Nature 1986a, 323:638.
3. Brenner, M. B., et al., Nature 1986, 322:145.
4. Bank., I., et al., Nature 1986. 322:179.
5. Davis, M. M., et al., Nature 1988. 334:395.
6. Crews, S., et al., Cell 1981. 25:59.
7. Concannon, P., et al., Proc. Natl. Acad. Sci. USA. 1986. 83:6598.
8. Kimura, N., et al., Eur. J. Immunol. 1987. 17:375.

9. Wilson, R. K., et al., Immunological Reviews 1988c. 101:149.

10. Chirgwin, J. M., et al. Biochemistry 1979. 18:5294.

11. Chomczynski, P., et al., Anal. Biochem. 1987. 162:156.

12. Saiki, R. K., et al., Science 1988. 239:487.

13. Loh, E. Y., et al., Science 1989. 243:217.

14. Sanger, F., et al., Proc. Natl. Acad. Sci. USA 1977. 74:5463.

15. Lipman, D. J., et al., Science 1985. 227:1435.

16. Kozak, M., Nucl. Acids Res. 1984. 12:857.

17. Kyte, J., et al., R. F., J. Mol. Biol. 1982. 157:105.

18. Triebel, F., et al., J. Immun. 1988. 140:300.

19. Feinberg, A. P., et. al., Anal. Bichem. 1983. 132:6.

20. Mengle-Gaw, L., et al., The EMBO Journal, 1987. 6:2273.

21. Klein, M. H., et al., Proc. Natl. Acad. Sci. USA 1987. 84:6884.

22. Yoshikai, Y., et al., J. Exp. Med. 1986. 164:90.

23. Wandenbark, A., et al , Nature, 341, 541.

24. Janeway, C., Nature, 341, 482.

25. Ci, Y., J. Exp. Mad., 171, 221.

26. Acha-Orbea, H., EMBO Journal, 1990,9, 12, 3815.

27. Kappler, J., Science 244, 811.

28. Choi, Y., PNAS, 86, 8941.

29. Nitta T. et al., Science 1990, 249, 672.

30. Sottini A. et al., Eur. J. Immunol., 1991, 21, 461.

31. Hinkkanen A. et al., Immunogenetics, 1989, 29, 131.

32. Bernard O. et al., Oncogene, 1988, 2, 195.

33. Sinha N. et al., Nucleic Acids Res. 1984, 12, 4539.

---

We claim:

1. An isolated nucleic acid coding for a variable region of an α chain of human T lymphocyte receptor, said nucleic acid consisting of a nucleotide sequence chosen from one of the nucleotide sequences of SEQ. ID. Nos. 4, 6, or 8.

2. An isolated nucleic acid of claim 1 selected from the group consisting of the nucleotide sequence of 1 to 467 of SEQ. ID No: 6 and 1 to 151 of SEQ ID No: 8.

3. A peptide coded by any one of the nucleic acids as defined in claim 1.

4. An expression vector containing a nucleic acid coding for one of the peptides as defined in claim 3.

* * * * *

SEQUENCE LISTING (1) GENERAL INFORMATION:

(iii) NUMBER OF SEQUENCES: 62

(2) INFORMATION FOR SEQ ID NO: 1:

(i) SEQUENCE CHARACTERISTICS:
      (A) LENGTH: 371
      (B) TYPE: NUCLEOTIDE
      (C) STRANDEDNESS: DOUBLE
      (D) TOPOLOGY: LINEAR (ii) MOLECULE TYPE: cDNA TO mRNA (vi) ORIGINAL SOURCE:
      (A) ORGANISM: HUMAN
      (B) STRAIN:
      (C) INDIVIDUAL ISOLATE:
      (D) DEVELOPMENTAL STAGE:
      (E) HAPLOTYPE:
      (F) TISSUE TYPE:
      (G) CELL TYPE:
      (H) CELL LINE: HUMAN T LYMPHOCYTE
      (I) ORGANELLE:

(ix) FEATURE:
      (A) NAME/KEY: IGR a 02
      (B) LOCATION:
      (C) IDENTIFICATION METHOD:
      (D) OTHER INFORMATION: SEQUENCE V Alpha w24

(xi) SEQUENCE DESCRIPTION: SEQ ID NO:1:

```
        AGTCAACTTC TGGGAGCAGT CTCTGCAGAA TAAAA ATG AAA AAG CAT         47
                                              Met Lys Lys His
                                              1

CTG ACG ACC TTC TTG GTG ATT TTG TGG CTT TAT TTT TAT AGG GGG AAT         95
Leu Thr Thr Phe Leu Val Ile Leu Trp Leu Tyr Phe Tyr Arg Gly Asn
5               10                  15                  20

GGC AAA AAC CAA GTG GAG CAG AGT CCT CAG TCC CTG ATC ATC CTG GAG        143
Gly Lys Asn Gln Val Glu Gln Ser Pro Gln Ser Leu Ile Ile Leu Glu
            25                  30                  35

GGA AAG AAC TGC ACT CTT CAA TGC AAT TAT ACA GTG AGC CCC TTC AGC        191
Gly Lys Asn Cys Thr Leu Gln Cys Asn Tyr Thr Val Ser Pro Phe Ser
        40                  45                  50

AAC TTA AGG TGG TAT AAG CAA GAT ACT GGG AGA GGT CCT GTT TCC CTG        239
Asn Leu Arg Trp Tyr Lys Gln Asp Thr Gly Arg Gly Pro Val Ser Leu
            55                  60                  65
```

```
ACA ATC ATG ACT TTC AGT GAG AAC ACA AAG TCG AAC GGA AGA TAT ACA              287
Thr Ile Met Thr Phe Ser Glu Asn Thr Lys Ser Asn Gly Arg Tyr Thr
    70              75                  80

GCA ACT CTG GAT GCA GAC ACA AAG CAA AGC TCT CTG CAC ATC ACA GCC              335
Ala Thr Leu Asp Ala Asp Thr Lys Gln Ser Ser Leu His Ile Thr Ala
85              90                  95                 100

TCC CAG CTC AGC GAT TCA GCC TCC TAC ATC TGT GTG                              371
Ser Gln Leu Ser Asp Ser Ala Ser Tyr Ile Cys Val
                105                 110
```

(2) INFORMATION FOR SEQ ID NO: 2:

(i) SEQUENCE CHARACTERISTICS:
        (A) LENGTH: 400
        (B) TYPE: NUCLEOTIDE
        (C) STRANDEDNESS: DOUBLE
        (D) TOPOLOGY: LINEAR (ii) MOLECULE TYPE: cDNA TO mRNA (vi) ORIGINAL SOURCE:
        (A) ORGANISM: HUMAN
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE: HUMAN T LYMPHOCYTE
        (I) ORGANELLE:

(ix) FEATURE:
        (A) NAME/KEY: IGR a 03
        (B) LOCATION:
        (C) IDENTIFICATION METHOD:
        (D) OTHER INFORMATION: SEQUENCE V Alpha w 25

(xi) SEQUENCE DESCRIPTION: SEQ ID NO:2:

```
                    GACTCTAAGC CCAAGAGAGT TTCTTGAAGC AAAAAAAAA                 40

AAAACCCATT CAGGAAATAA TTCTTTGCTG ATAAGG ATG CTC CTT GAA CAT TTA              94
                                       Met Leu Leu Glu His Leu
                                         1               5

TTA ATA ATC TTG TGG ATG CAG CTG ACA TGG GTC AGT GGT CAA CAG CTG             142
Leu Ile Ile Leu Trp Met Gln Leu Thr Trp Val Ser Gly Gln Gln Leu
            10                  15                  20

AAT CAG AGT CCT CAA TCT ATG TTT ATC CAG GAA GGA GAA GAT GTC TCC             190
Asn Gln Ser Pro Gln Ser Met Phe Ile Gln Glu Gly Glu Asp Val Ser
            25                  30                  35

ATG AAC TGC ACT TCT TCA AGC ATA TTT AAC ACC TGG CTA TGG TAC AAG             238
Met Asn Cys Thr Ser Ser Ser Ile Phe Asn Thr Trp Leu Trp Tyr Lys
        40                  45                  50

CAG GAC CCT GGG GAA GGT CCT GTC CTC TTG ATA GCC TTA TAT AAG GCT             286
Gln Asp Pro Gly Glu Gly Pro Val Leu Leu Ile Ala Leu Tyr Lys Ala
55                  60                  65                  70

GGT GAA TTG ACC TCA AAT GGA AGA CTG ACT GCT CAG TTT GGT ATA ACC             334
Gly Glu Leu Thr Ser Asn Gly Arg Leu Thr Ala Gln Phe Gly Ile Thr
                75                  80                  85

AGA AAG GAC AGC TTC CTG AAT ATC TCA GCA TCC ATA CCT AGT GAT GTA             382
Arg Lys Asp Ser Phe Leu Asn Ile Ser Ala Ser Ile Pro Ser Asp Val
            90                  95                 100

GGC ATC TAC TTC TGT GCT                                                     400
Gly Ile Tyr Phe Cys Ala
            105
```

(2) INFORMATION FOR SEQ ID NO: 3:

```
    (i) SEQUENCE CHARACTERISTICS:
        (A) LENGTH: 339
        (B) TYPE: NUCLEOTIDE
        (C) STRANDEDNESS: DOUBLE
        (D) TOPOLOGY: LINEAR (ii) MOLECULE TYPE: cDNA to mRNA (vi) ORIGINAL SOURCE:
        (A) ORGANISM: HUMAN
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE: HUMAN T LYMPHOCYTE
        (I) ORGANELLE:

(ix) FEATURE:
        (A) NAME/KEY: IGR a 04
        (B) LOCATION:
        (C) IDENTIFICATION METHOD:
        (D) OTHER INFORMATION: SEQUENCE V Alpha w26

(xi) SEQUENCE DESCRIPTION: SEQ ID NO:3:

AGCTAAGGG ATG GAG ACT GTT CTG CAA GTA CTC CTA GGG ATA TTG GGG         48
             Met Glu Thr Val Leu Gln Val Leu Leu Gly Ile Leu Gly
               1               5                  10

TTC CAA GCA GCC TGG GTC AGT AGC CAA GAA CTG GAG CAG AGT CCT CAG         96
Phe Gln Ala Ala Trp Val Ser Ser Gln Glu Leu Glu Gln Ser Pro Gln
         15              20                  25

TCC TTG ATC GTC CAA GAG GGA AAG AAT CTC ACC ATA AAC TGC ACG TCA        144
Ser Leu Ile Val Gln Glu Gly Lys Asn Leu Thr Ile Asn Cys Thr Ser
 30              35                  40                  45

TCA AAG ACG TTA TAT GGC TTA TAC TGG TAT AAG CAA AAG TAT GGT GAA        192
Ser Lys Thr Leu Tyr Gly Leu Tyr Trp Tyr Lys Gln Lys Tyr Gly Glu
                 50                  55                  60

GGT CTT ATC TTC TTG ATG ATG CTA CAG AAA GGT GGG GAA GAG AAA AGT        240
Gly Leu Ile Phe Leu Met Met Leu Gln Lys Gly Gly Glu Glu Lys Ser
                 65                  70                  75

CAT GAA AAG ATA ACT GCC AAG TTG GAT GAG AAA AAG CAG CAA AGT TCC        288
His Glu Lys Ile Thr Ala Lys Leu Asp Glu Lys Lys Gln Gln Ser Ser
         80                  85                  90

CTG CAT ATC ACA GCC TCC CAG CCC AGC CAT GCA GGC ATC TAC CTC TGT        336
Leu His Ile Thr Ala Ser Gln Pro Ser His Ala Gly Ile Tyr Leu Cys
     95                 100                 105

GGA                                                                    339
Gly
110

(2) INFORMATION FOR SEQ ID NO: 4:

(i) SEQUENCE CHARACTERISTICS:
        (A) LENGTH: 335
        (B) TYPE: NUCLEOTIDE
        (C) STRANDEDNESS: DOUBLE
        (D) TOPOLOGY: LINEAR (ii) MOLECULE TYPE: cDNA to mRNA (vi) ORIGINAL SOURCE:
        (A) ORGANISM: HUMAN
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE: HUMAN T LYMPHOCYTE
        (I) ORGANELLE:
```

```
    (ix) FEATURE:
          (A) NAME/KEY:  IGR a 05
          (B) LOCATION:
          (C) IDENTIFICATION METHOD:
          (D) OTHER INFORMATION:  SEQUENCE V Alpha w27

(xi) SEQUENCE DESCRIPTION: SEQ ID NO:4:

AGAAAAAAAA AATGAAGAAG CTACTAGCAA TGATCCTGTG GCTTCAACTA        50

GACCGGTTAA GTGGAGAGCT GAAAGTG GAA CAA AAC CCT CTG TTC     95
                                            Glu Gln Asn Pro Leu Phe
                                             1               5

CTG AGC ATG CAG GAG GGA AAA AAC TAT ACC ATC TAC TGC AAT TAT TCA        143
Leu Ser Met Gln Glu Gly Lys Asn Tyr Thr Ile Tyr Cys Asn Tyr Ser
        10              15              20

ACC ACT TCA GAC AGA CTG TAT TGG TAC AGG CAG GAT CCT GGG AAA AGT        191
Thr Thr Ser Asp Arg Leu Tyr Trp Tyr Arg Gln Asp Pro Gly Lys Ser
            25              30              35

CTG GAA TCT CTG TTT GTG TTG CTA TCA AAT GGA GCA GTG AAG CAG GAG        239
Leu Glu Ser Leu Phe Val Leu Leu Ser Asn Gly Ala Val Lys Gln Glu
40              45              50

GGA CGA TTA ATG GCC TCA CTT GAT ACC AAA GCC CGT CTC AGC ACC CTC        287
Gly Arg Leu Met Ala Ser Leu Asp Thr Lys Ala Arg Leu Ser Thr Leu
55              60              65              70

CAC ATC ACA GCT GCC GTG CAT GAC CTC TCT GCC ACC TAC TTC TGT GCC        335
His Ile Thr Ala Ala Val His Asp Leu Ser Ala Thr Tyr Phe Cys Ala
                75              80              85

(2) INFORMATION FOR SEQ ID NO: 5:

(i) SEQUENCE CHARACTERISTICS:
          (A) LENGTH: 361
          (B) TYPE: NUCLEOTIDE
          (C) STRANDEDNESS: DOUBLE
          (D) TOPOLOGY: LINEAR (ii) MOLECULE TYPE: cDNA to mRNA (vi) ORIGINAL SOURCE:
          (A) ORGANISM:  HUMAN
          (B) STRAIN:
          (C) INDIVIDUAL ISOLATE:
          (D) DEVELOPMENTAL STAGE:
          (E) HAPLOTYPE:
          (F) TISSUE TYPE:
          (G) CELL TYPE:
          (H) CELL LINE:  HUMAN T LYMPHOCYTE
          (I) ORGANELLE:

(ix) FEATURE:
          (A) NAME/KEY:  IGR a 07
          (B) LOCATION:
          (C) IDENTIFICATION METHOD:
          (D) OTHER INFORMATION:  SEQUENCE V Alpha w29

(xi) SEQUENCE DESCRIPTION: SEQ ID NO:5:

GAAGCTGACT GGATATTCTG GCAGGCCAAG G ATG GAG ACT CTC CTG         46
                                            Met Glu Thr Leu Leu
                                             1               5

AAA GTG CCT TCA GGC ACC TTG TTG TGG CAG TTG ACC TGG GTG GGA AGC         94
Lys Val Pro Ser Gly Thr Leu Leu Trp Gln Leu Thr Trp Val Gly Ser
        10              15              20

CAA CAA CCA GTG CAG AGT CCT CAA GCC GTG ATC CTC CGA GAA GGG GAA        142
Gln Gln Pro Val Gln Ser Pro Gln Ala Val Ile Leu Arg Glu Gly Glu
            25              30              35

GAT GCT GTC ACC AAC TGC AGT TCC TCC AAG GCT TTA TAT TCT GTA CAC        190
Asp Ala Val Thr Asn Cys Ser Ser Ser Lys Ala Leu Tyr Ser Val His
40              45              50
```

| TGG TAC AGG CAG AAG CAT GGT GAA GCA CCC GTC TTC CTG ATG ATA TTA | 238 |
| Trp Tyr Arg Gln Lys His Gly Glu Ala Pro Val Phe Leu Met Ile Leu | |
| 55 60 65 | |

| CTG AAG GGT GGA GAA CAG ATG CGT CGT GAA AAA ATA TCT GCT TCA TTT | 286 |
| Leu Lys Gly Gly Glu Gln Met Arg Arg Glu Lys Ile Ser Ala Ser Phe | |
| 70 75 80 85 | |

| AAT GAA AAA AAG CAG CAA AGC TCC CTG TAC CTT ACG GCC TCC CAG CTC | 334 |
| Asn Glu Lys Lys Gln Gln Ser Ser Leu Tyr Leu Thr Ala Ser Gln Leu | |
| 90 95 100 | |

| AGT TAC TCA GGA ACC TAC TTC TGC GGG | 361 |
| Ser Tyr Ser Gly Thr Tyr Phe Cys Gly | |
| 105 110 | |

(2) INFORMATION FOR SEQ ID NO: 6:

(i) SEQUENCE CHARACTERISTICS:
        (A) LENGTH: 569
        (B) TYPE: NUCLEOTIDE
        (C) STRANDEDNESS: DOUBLE
        (D) TOPOLOGY: LINEAR (ii) MOLECULE TYPE: cDNA to mRNA (vi) ORIGINAL SOURCE:
        (A) ORGANISM: HUMAN
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE: HUMAN T LYMPHOCYTE
        (I) ORGANELLE:

(ix) FEATURE:
        (A) NAME/KEY: IGR a 08
        (B) LOCATION:
        (C) IDENTIFICATION METHOD:
        (D) OTHER INFORMATION: SEQUENCE V Alpha 1

(xi) SEQUENCE DESCRIPTION: SEQ ID NO:6:

| | |
|---|---|
| TCAGTTTCTT | 10 |
| CTTCCTGCAG CTGGTTGAGT TCTTTCCAGA CAAAGACAAG TGACAAGAAT TAGAGGTTTA | 70 |
| AAAAGCAACC AGATTCATCT CAGCAGCTTT TGTAGTTTTA AATAAGCAAG GAGTTTCTCC | 130 |
| AGCGAAACTT CCTCACACCT CTTGGTCTTG GTCTCTTCAG ACACTTTCCT TCCTGTTCTC | 190 |
| TGGAGATCTT GCAGAAAAGA GCCTGCAGTG TTTCCCTTGC TCAGCC ATG CTC CTG | 245 |
|                                                           Met Leu Leu | |
|                                                                 1 | |

| GAG CTT ATC CCA CTG CTG GGG ATA CAT TTT GTC CTG AGA ACT GCC AGA | 293 |
| Glu Leu Ile Pro Leu Leu Gly Ile His Phe Val Leu Arg Thr Ala Arg | |
| 5 10 15 | |

| GCC CAG TCA GTG ACC CAG CCT GAC ATC CAC ATC ACT GTC TCT GAA GGA | 341 |
| Ala Gln Ser Val Thr Gln Pro Asp Ile His Ile Thr Val Ser Glu Gly | |
| 20 25 30 35 | |

| GCC TCA CTG GAG TTG AGA TGT AAC TAT TCC TAT GGG GCA ACA CCT TAT | 389 |
| Ala Ser Leu Glu Leu Arg Cys Asn Tyr Ser Tyr Gly Ala Thr Pro Tyr | |
| 40 45 50 | |

| CTC TTC TGG TAT GTC CAG TCC CCC GGC CAA GGC CTC CAG CTG CTC CTG | 437 |
| Leu Phe Trp Tyr Val Gln Ser Pro Gly Gln Gly Leu Gln Leu Leu Leu | |
| 55 60 65 | |

| AAG TAC TTT TCA GGA GAC ACT CTG GTT CAA GGC ATT AAA GGC TTT GAG | 485 |
| Lys Tyr Phe Ser Gly Asp Thr Leu Val Gln Gly Ile Lys Gly Phe Glu | |
| 70 75 80 | |

| GCT GAA TTT AAG AGG AGT CAA TCT TCC TTC AAC CTG AGG AAA CCC TCT | 533 |

```
Ala Glu Phe Lys Arg Ser Gln Ser Ser Phe Asn Leu Arg Lys Pro Ser
    85                  90                  95

GTG CAT TGG AGT GAT GCT GCT GAG TAC TTC TGT GCT                      569
Val His Trp Ser Asp Ala Ala Glu Tyr Phe Cys Ala
100             105                 110
```

(2) INFORMATION FOR SEQ ID NO: 7:

(i) SEQUENCE CHARACTERISTICS:
        (A) LENGTH: 330
        (B) TYPE: NUCLEOTIDE
        (C) STRANDEDNESS: DOUBLE
        (D) TOPOLOGY: LINEAR (ii) MOLECULE TYPE: cDNA to mRNA (vi) ORIGINAL SOURCE:
        (A) ORGANISM: HUMAN
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE: HUMAN T LYMPHOCYTE
        (I) ORGANELLE:

(ix) FEATURE:
        (A) NAME/KEY: IGR a 09
        (B) LOCATION:
        (C) IDENTIFICATION METHOD:
        (D) OTHER INFORMATION: SEQUENCE V Alpha 2

(xi) SEQUENCE DESCRIPTION: SEQ ID NO:7:

```
AAA TCC TTG AGA GTT TTA CTA GTG ATC CTG TGG CTT CAG CTG AGC CGG      48
Lys Ser Leu Arg Val Leu Leu Val Ile Leu Trp Leu Gln Leu Ser Arg
1               5                   10                  15

GTT TGG AGC CAA CAG AAG GAG GTG GAG CAG AAT TCT GGA CCC CTC AGT      96
Val Trp Ser Gln Gln Lys Glu Val Glu Gln Asn Ser Gly Pro Leu Ser
                20                  25                  30

GTT CCA GAG GGA GCC ATT GCC TCT CTC AAC TGC ACT TAC AGT GAC CGA     144
Val Pro Glu Gly Ala Ile Ala Ser Leu Asn Cys Thr Tyr Ser Asp Arg
            35                  40                  45

GGT TCC CAG TCC TTC TTC TGG TAC AGA CAA TAT TCT GGG AAA AGC CCT     192
Gly Ser Gln Ser Phe Phe Trp Tyr Arg Gln Tyr Ser Gly Lys Ser Pro
        50                  55                  60

GAG TTG ATA ATG TCC ATA TAC TCC AAT GGT GAC AAA GAA GAT GGA AGG     240
Glu Leu Ile Met Ser Ile Tyr Ser Asn Gly Asp Lys Glu Asp Gly Arg
65                  70                  75                  80

TTT ACA GCA CAG CTC AAT AAA GCC AGC CAG TAT GTT TCT CTG CTC ATC     288
Phe Thr Ala Gln Leu Asn Lys Ala Ser Gln Tyr Val Ser Leu Leu Ile
                85                  90                  95

AGA GAC TCC CAG CCC AGT GAT TCA GCC ACC TAC CTC TGT GCC             330
Arg Asp Ser Gln Pro Ser Asp Ser Ala Thr Tyr Leu Cys Ala
            100                 105                 110
```

(2) INFORMATION FOR SEQ ID NO: 8:

(i) SEQUENCE CHARACTERISTICS:
        (A) LENGTH: 400
        (B) TYPE: NUCLEOTIDE
        (C) STRANDEDNESS: DOUBLE
        (D) TOPOLOGY: LINEAR (ii) MOLECULE TYPE: cDNA to mRNA (vi) ORIGINAL SOURCE:
        (A) ORGANISM: HUMAN
        (B) STRAIN:
        (C) INDIVIDUAL ISOLATE:

```
               (D) DEVELOPMENTAL STAGE:
               (E) HAPLOTYPE:
               (F) TISSUE TYPE:
               (G) CELL TYPE:
               (H) CELL LINE:  HUMAN T LYMPHOCYTE
               (I) ORGANELLE:

(ix) FEATURE:
               (A) NAME/KEY:  IGR a 10
               (B) LOCATION:
               (C) IDENTIFICATION METHOD:
               (D) OTHER INFORMATION:  SEQUENCE V Alpha 5

(xi) SEQUENCE DESCRIPTION: SEQ ID NO:8:

GCCAAACAGA ATGGCTTTTT GGCTGAGAAG GCTGGGTCTA CATTTCAGGC         50

CACATTTGGG GAGACGA ATG GAG TCA TCC CTG GGA GGT GTT TTG         94
                               Met Glu Ser Ser Leu Gly Gly Val Leu
                                1               5

CTG ATT TTG TGG CTT CAA GTG GAC TGG GTG AAG AGC CAA AAG ATA GAA             142
Leu Ile Leu Trp Leu Gln Val Asp Trp Val Lys Ser Gln Lys Ile Glu
 10              15                  20                  25

CAG AAT TCC GAG GCC CTG AAC ATT CAG GAG GGT AAA ACG GCC ACC CTG             190
Gln Asn Ser Glu Ala Leu Asn Ile Gln Glu Gly Lys Thr Ala Thr Leu
                 30                  35                  40

ACC TGC AAC TAT ACA AAC TAT TCT CCA GCA TAC TTA CAG TGG TAC CGA             238
Thr Cys Asn Tyr Thr Asn Tyr Ser Pro Ala Tyr Leu Gln Trp Tyr Arg
             45                  50                  55

CAA GAT CCA GGA AGA GGC CCT GTT TTC TTG CTA CTC ATA CGT GAA AAT             286
Gln Asp Pro Gly Arg Gly Pro Val Phe Leu Leu Leu Ile Arg Glu Asn
         60                  65                  70

GAG AAA GAA AAA AGG AAA GAA AGA CTG AAG GTC ACC TTT GAT ACC ACC             334
Glu Lys Glu Lys Arg Lys Glu Arg Leu Lys Val Thr Phe Asp Thr Thr
 75                  80                  85

CTT AAA CAG AGT TTG TTT CAT ATC ACA GCC TCC CAG CCT GCA GAC TCA             382
Leu Lys Gln Ser Leu Phe His Ile Thr Ala Ser Gln Pro Ala Asp Ser
 90                  95                 100                 105

GCT ACC TAC CTC TGT GCT                                                      400
Ala Thr Tyr Leu Cys Ala
                 110

(2) INFORMATION FOR SEQ ID NO: 9:

(i) SEQUENCE CHARACTERISTICS:
               (A) LENGTH: 386
               (B) TYPE: NUCLEOTIDE
               (C) STRANDEDNESS: DOUBLE
               (D) TOPOLOGY: LINEAR (ii) MOLECULE TYPE: cDNA to mRNA (vi) ORIGINAL SOURCE:
               (A) ORGANISM:  HUMAN
               (B) STRAIN:
               (C) INDIVIDUAL ISOLATE:
               (D) DEVELOPMENTAL STAGE:
               (E) HAPLOTYPE:
               (F) TISSUE TYPE:
               (G) CELL TYPE:
               (H) CELL LINE:  HUMAN T LYMPHOCYTE
               (I) ORGANELLE:

(ix) FEATURE:
               (A) NAME/KEY:  IGR a 11
               (B) LOCATION:
               (C) IDENTIFICATION METHOD:
               (D) OTHER INFORMATION:  SEQUENCE V Alpha 7

(xi) SEQUENCE DESCRIPTION: SEQ ID NO:9:

GCCTTCTGCA GACTCCAATG GCTCAGGAAC TGGGAATGCA GTGCCAGGCT          50
```

```
                    CGTGGTATCC TGCAGCAG ATG TGG GGA GTT TTC CTT CTT TAT GTT        95
                                       Met Trp Gly Val Phe Leu Leu Tyr Val
                                        1               5

TCC ATG AAG ATG GGA GGC ACT ACA GGA CAA AAC ATT GAC CAG CCC ACT                   143
Ser Met Lys Met Gly Gly Thr Thr Gly Gln Asn Ile Asp Gln Pro Thr
 10              15                  20                  25

GAG ATG ACA GCT ACG GAA GGT GCC ATT GTC CAG ATC AAC TGC ACG TAC                   191
Glu Met Thr Ala Thr Glu Gly Ala Ile Val Gln Ile Asn Cys Thr Tyr
                 30                  35                  40

CAG ACA TCT GGG TTC AAC GGG CTG TTC TGG TAC CAG CAA CAT GCT GGC                   239
Gln Thr Ser Gly Phe Asn Gly Leu Phe Trp Tyr Gln Gln His Ala Gly
             45                  50                  55

GAA GCA CCC ACA TTT CTG TCT TAC AAT GTT CTG GAT GGT TTG GAG GAG                   287
Glu Ala Pro Thr Phe Leu Ser Tyr Asn Val Leu Asp Gly Leu Glu Glu
         60                  65                  70

AAA GGT CGT TTT TCT TCA TTC CTT AGT CGG TCT AAA GGG TAC AGT TAC                   335
Lys Gly Arg Phe Ser Ser Phe Leu Ser Arg Ser Lys Gly Tyr Ser Tyr
     75                  80                  85

CTC CTT TTG AAG GAG CTC CAG ATG AAA GAC TCT GCC TCT TAC CTC TGT                   383
Leu Leu Leu Lys Glu Leu Gln Met Lys Asp Ser Ala Ser Tyr Leu Cys
 90              95                 100                 105

GCT                                                                               386
Ala (2) INFORMATION FOR SEQ ID NO: 10:

(i) SEQUENCE CHARACTERISTICS:
        (A) LENGTH: 383
        (B) TYPE: NUCLEOTIDE
        (C) STRANDEDNESS: DOUBLE
        (D) TOPOLOGY: LINEAR (ii) MOLECULE TYPE: cDNA TO mRNA (vi) ORIGINAL SOURCE:
        (A) ORGANISM:  HUMAN
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:  HUMAN T LYMPHOCYTE
        (I) ORGANELLE:

(ix) FEATURE:
        (A) NAME/KEY:  IGR a 12
        (B) LOCATION:
        (C) IDENTIFICATION METHOD:
        (D) OTHER INFORMATION:  SEQUENCE V Alpha 22

(xi) SEQUENCE DESCRIPTION: SEQ ID NO:10:

TGTGACTTCT TCATGTTAAG GATCAAGACC ATTATTTGGG TAACACACTA                 50

AAG ATG AAC TAT TCT CCA GGC TTA GTA TCT CTG ATA CTC TTA CTG                95
            Met Asn Tyr Ser Pro Gly Leu Val Ser Leu Ile Leu Leu Leu
             1               5                  10

CTT GGA AGA ACC CGT GGA GAT TCA GTG ACC CAG ATG GAA GGG CCA GTG                   143
Leu Gly Arg Thr Arg Gly Asp Ser Val Thr Gln Met Glu Gly Pro Val
 15              20                  25                  30

ACT CTC TCA GAA GAG GCC TTC CTG ACT ATA AAC TGC ACG TAC ACA GCC                   191
Thr Leu Ser Glu Glu Ala Phe Leu Thr Ile Asn Cys Thr Tyr Thr Ala
                 35                  40                  45

ACA GGA TAC CCT TCC CTT TTC TGG TAT GTC CAA TAT CCT GGA GAA GGT                   239
Thr Gly Tyr Pro Ser Leu Phe Trp Tyr Val Gln Tyr Pro Gly Glu Gly
             50                  55                  60
```

```
CTA CAG CTC CTC CTG AAA GCC ACG AAG GCT GAT GAC AAG GGA AGC AAC     287
Leu Gln Leu Leu Leu Lys Ala Thr Lys Ala Asp Asp Lys Gly Ser Asn
            65                  70                  75

AAA GGT TTT GAA GCC ACA TAC CGT AAA GAA ACC ACT TCT TTC CAC TTG     335
Lys Gly Phe Glu Ala Thr Tyr Arg Lys Glu Thr Thr Ser Phe His Leu
     80                  85                  90

GAG AAA GGC TCA GTT CAA GTG TCA GAC TCA GCG GTG TAC TTC TGT GCT     383
Glu Lys Gly Ser Val Gln Val Ser Asp Ser Ala Val Tyr Phe Cys Ala
 95              100                 105                 110

(2) INFORMATION FOR SEQ ID NO: 11:

(i) SEQUENCE CHARACTERISTICS:
        (A) LENGTH: 364
        (B) TYPE: NUCLEOTIDE
        (C) STRANDEDNESS: DOUBLE
        (D) TOPOLOGY: LINEAR (ii) MOLECULE TYPE: cDNA to mRNA (vi) ORIGINAL SOURCE:
        (A) ORGANISM: HUMAN
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE: HUMAN T LYMPHOCYTE
        (I) ORGANELLE:

(ix) FEATURE:
        (A) NAME/KEY: IGR a 13
        (B) LOCATION:
        (C) IDENTIFICATION METHOD:
        (D) OTHER INFORMATION: SEQUENCE V Alpha 16

(xi) SEQUENCE DESCRIPTION: SEQ ID NO:11:

AATCCCGCCC GCCGTGAGCT TAGCTGGAGC C ATG GCC TCT GCA CCC       46
                                             Met Ala Ser Ala Pro
                                              1               5

ATC TCG ATG CTT GCG ATG CTC TTC ACA TTG AGT GGG CTG AGA GCT CAG      94
Ile Ser Met Leu Ala Met Leu Phe Thr Leu Ser Gly Leu Arg Ala Gln
             10                  15                  20

TCA GTG GCT CAG CCG GAA GAT CAG GTC AAC GTT GCT GAA GGG AAT CCT     142
Ser Val Ala Gln Pro Glu Asp Gln Val Asn Val Ala Glu Gly Asn Pro
             25                  30                  35

CTG ACT GTG AAA TGC ACC TAT TCA GTC TCT GGA AAC CCT TAT CTT TTT     190
Leu Thr Val Lys Cys Thr Tyr Ser Val Ser Gly Asn Pro Tyr Leu Phe
         40                  45                  50

TGG TAT GTT CAA TAC CCC AAC CGA GGC CTC CAG TTC CTT CTG AAA TAC     238
Trp Tyr Val Gln Tyr Pro Asn Arg Gly Leu Gln Phe Leu Leu Lys Tyr
     55                  60                  65

ATC ACA GGG GAT AAC CTG GTT AAA GGC AGC TAT GGC TTT GAA GCT GAA     286
Ile Thr Gly Asp Asn Leu Val Lys Gly Ser Tyr Gly Phe Glu Ala Glu
 70                  75                  80                  85

TTT AAC AAG AGC CAA ACC TCC TTC CAC CTG AAG AAA CCA TCT GCC CTT     334
Phe Asn Lys Ser Gln Thr Ser Phe His Leu Lys Lys Pro Ser Ala Leu
                 90                  95                 100

GTG AGC GAC TCC GCT TTG TAC TTC TGT GCT                              364
Val Ser Asp Ser Ala Leu Tyr Phe Cys Ala
            105                 110

(2) INFORMATION FOR SEQ ID NO: 12:

(i) SEQUENCE CHARACTERISTICS:
        (A) LENGTH: 263
        (B) TYPE: NUCLEOTIDE
```

(C) STRANDEDNESS: DOUBLE
            (D) TOPOLOGY: LINEAR (ii) MOLECULE TYPE: cDNA to mRNA (vi) ORIGINAL SOURCE:
            (A) ORGANISM: HUMAN
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE: HUMAN T LYMPHOCYTE
            (I) ORGANELLE:

(ix) FEATURE:
            (A) NAME/KEY: Ja 01
            (B) LOCATION:
            (C) IDENTIFICATION METHOD:
            (D) OTHER INFORMATION: SEQUENCE J Alpha (xi) SEQUENCE DESCRIPTION: SEQ ID NO:12:

```
CCTTCAAGGA AAATTAAGGC AAATAGAATT GGGCTGGGGA GTTGCTACTT ATTAGTATTC      60

CTCCCACGTT CTAACCTAAT TATAAGGAGG TTGTTTTGGC CATGGGCAGT CATCTCAGGT     120

TTTGTTTTCC TGCTTTCCTC CCTAACCTCC ACCTGTCTTC CTAGAGGCCT GAGTCAAGGT     180

TATTGCAATA GCACTAAAGA CTGTGT AAC ACC AAT GCA GGC AAA TCA ACC TTT     233
                             Asn Thr Asn Ala Gly Lys Ser Thr Phe
                              1                   5

GGG GAT GGG ACT ACG CTC ACT GTG AAG CCA                              263
Gly Asp Gly Thr Thr Leu Thr Val Lys Pro
 10                  15
```

(2) INFORMATION FOR SEQ ID NO: 13:

(i) SEQUENCE CHARACTERISTICS:
            (A) LENGTH: 277
            (B) TYPE: NUCLEOTIDE
            (C) STRANDEDNESS: DOUBLE
            (D) TOPOLOGY: LINEAR (ii) MOLECULE TYPE: cDNA to mRNA (vi) ORIGINAL SOURCE:
            (A) ORGANISM: HUMAN
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE: HUMAN T LYMPHOCYTE
            (I) ORGANELLE:

(ix) FEATURE:
            (A) NAME/KEY: Ja 02
            (B) LOCATION:
            (C) IDENTIFICATION METHOD:
            (D) OTHER INFORMATION: SEQUENCE J Alpha (xi) SEQUENCE DESCRIPTION: SEQ ID NO:13:

```
AAGGACACAG ACTGCCTGCA TGAAGGCTGG AGCTGGGCCC AGGATGAGGA AAGGCCTCAG      60

GAAGGAAGGG CTGACACGAA ATAAGGAATA CCATGGCATT CATGAGATGT GCGTCTGAAT     120

CCTCTCTCTT GCCTGAGAAG CTTTAGCTTC CACCTTGAGA CACAAAACAT GTGGTTATGA     180

AGAGATGACA AGGTTTTTGT AAAAGAATGA GCCATTGTGG ATA GGC TTT GGG AAT      235
                                              Ile Gly Phe Gly Asn
                                               1               5

GTG CTG CAT TGC GGG TCC GGC ACT CAA GTG ATT GTT TTA CCA              277
Val Leu His Cys Gly Ser Gly Thr Gln Val Ile Val Leu Pro
```

(2) INFORMATION FOR SEQ ID NO: 15:

(i) SEQUENCE CHARACTERISTICS:
(A) LENGTH: 60
(B) TYPE: NUCLEOTIDE
(C) STRANDEDNESS: DOUBLE
(D) TOPOLOGY: LINEAR (ii) MOLECULE TYPE: cDNA to mRNA (vi) ORIGINAL SOURCE:
(A) ORGANISM: HUMAN
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE: HUMAN T LYMPHOCYTE
(I) ORGANELLE:

(ix) FEATURE:
(A) NAME/KEY: Ja 04
(B) LOCATION:
(C) IDENTIFICATION METHOD:
(D) OTHER INFORMATION: SEQUENCE J Alpha (xi) SEQUENCE DESCRIPTION: SEQ ID NO:15:

```
TA GAT ACT GGA GGC TTC AAA ACT ATC TTT GGA GCA GGA ACA AGA CTA        47
   Asp Thr Gly Gly Phe Lys Thr Ile Phe Gly Ala Gly Thr Arg Leu
   1               5                   10                  15

TTT GTT AAA GCA A                                                     60
Phe Val Lys Ala
```

(2) INFORMATION FOR SEQ ID NO: 16:

(i) SEQUENCE CHARACTERISTICS:
(A) LENGTH: 59
(B) TYPE: NUCLEOTIDE
(C) STRANDEDNESS: DOUBLE
(D) TOPOLOGY: LINEAR (ii) MOLECULE TYPE: cDNA to mRNA (vi) ORIGINAL SOURCE:
(A) ORGANISM: HUMAN
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE: HUMAN T LYMPHOCYTE
(I) ORGANELLE:

(ix) FEATURE:
(A) NAME/KEY: Ja 05
(B) LOCATION:
(C) IDENTIFICATION METHOD:
(D) OTHER INFORMATION: SEQUENCE J Alpha (xi) SEQUENCE DESCRIPTION: SEQ ID NO:16:

```
C CTA ACT GGG GCA AAC AAC GTC TTC TTT GGG ACT GGA ACG AGA CTC         46
  Leu Thr Gly Ala Asn Asn Val Phe Phe Gly Thr Gly Thr Arg Leu
  1               5                   10                  15

ACC GTT CTT CCC T                                                     59
Thr Val Leu Pro
```

(2) INFORMATION FOR SEQ ID NO: 17:

(i) SEQUENCE CHARACTERISTICS:

(A) LENGTH: 60
        (B) TYPE: NUCLEOTIDE
        (C) STRANDEDNESS: DOUBLE
        (D) TOPOLOGY: LINEAR (ii) MOLECULE TYPE: cDNA to mRNA (vi) ORIGINAL SOURCE:
        (A) ORGANISM: HUMAN
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE: HUMAN T LYMPHOCYTE
        (I) ORGANELLE:

(ix) FEATURE:
        (A) NAME/KEY: Ja 06
        (B) LOCATION:
        (C) IDENTIFICATION METHOD:
        (D) OTHER INFORMATION: SEQUENCE J Alpha (xi) SEQUENCE DESCRIPTION: SEQ ID NO:17:

```
AT GGA GGA AGC CAA GGA AAT CTC ATC TTT GGA AAA GGC ACT AAA CTC        47
   Gly Gly Ser Gln Gly Asn Leu Ile Phe Gly Lys Gly Thr Lys Leu
   1               5                  10                  15

TCT GTT AAA CCA A                                                     60
Ser Val Lys Pro
```

(2) INFORMATION FOR SEQ ID NO: 18:

(i) SEQUENCE CHARACTERISTICS:
        (A) LENGTH: 56
        (B) TYPE: NUCLEOTIDE
        (C) STRANDEDNESS: DOUBLE
        (D) TOPOLOGY: LINEAR (ii) MOLECULE TYPE: cDNA to mRNA (vi) ORIGINAL SOURCE:
        (A) ORGANISM: HUMAN
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE: HUMAN T LYMPHOCYTE
        (I) ORGANELLE:

(ix) FEATURE:
        (A) NAME/KEY: Ja 07
        (B) LOCATION:
        (C) IDENTIFICATION METHOD:
        (D) OTHER INFORMATION: SEQUENCE J Alpha (xi) SEQUENCE DESCRIPTION: SEQ ID NO:18:

```
GGA GCC AAT AGT AAG CTG ACA TTT GGA AAA GGA ATA ACT CTG AGT GTT       48
Gly Ala Asn Ser Lys Leu Thr Phe Gly Lys Gly Ile Thr Leu Ser Val
1               5                  10                  15

AGA CCA GA                                                            56
Arg Pro
```

(2) INFORMATION FOR SEQ ID NO: 19:

(i) SEQUENCE CHARACTERISTICS:
        (A) LENGTH: 57
        (B) TYPE: NUCLEOTIDE
        (C) STRANDEDNESS: DOUBLE
        (D) TOPOLOGY: LINEAR (ii) MOLECULE TYPE: cDNA to mRNA

```
        (vi) ORIGINAL SOURCE:
              (A) ORGANISM: HUMAN
              (B) STRAIN:
              (C) INDIVIDUAL ISOLATE:
              (D) DEVELOPMENTAL STAGE:
              (E) HAPLOTYPE:
              (F) TISSUE TYPE:
              (G) CELL TYPE:
              (H) CELL LINE: HUMAN T LYMPHOCYTE
              (I) ORGANELLE:

(ix) FEATURE:
              (A) NAME/KEY: Ja 08
              (B) LOCATION:
              (C) IDENTIFICATION METHOD:
              (D) OTHER INFORMATION: SEQUENCE J Alpha (xi) SEQUENCE DESCRIPTION: SEQ ID NO:19:

CT GGT GGC TAC AAT AAG CTG ATT TTT GGA GCA GGG ACC AGG CTG GCT         47
   Gly Gly Tyr Asn Lys Leu Ile Phe Gly Ala Gly Thr Arg Leu Ala
   1               5                   10                  15

GTA CAC CCA T                                                          57
Val His Pro (2) INFORMATION FOR SEQ ID NO: 20:

(i) SEQUENCE CHARACTERISTICS:
              (A) LENGTH: 50
              (B) TYPE: NUCLEOTIDE
              (C) STRANDEDNESS: DOUBLE
              (D) TOPOLOGY: LINEAR (ii) MOLECULE TYPE: cDNA to mRNA (vi) ORIGINAL SOURCE:
              (A) ORGANISM: HUMAN
              (B) STRAIN:
              (C) INDIVIDUAL ISOLATE:
              (D) DEVELOPMENTAL STAGE:
              (E) HAPLOTYPE:
              (F) TISSUE TYPE:
              (G) CELL TYPE:
              (H) CELL LINE: HUMAN T LYMPHOCYTE
              (I) ORGANELLE:

(ix) FEATURE:
              (A) NAME/KEY: Ja 09
              (B) LOCATION:
              (C) IDENTIFICATION METHOD:
              (D) OTHER INFORMATION: SEQUENCE J Alpha (xi) SEQUENCE DESCRIPTION: SEQ ID NO:20:

T GGA AAC AAG CTG GTC TTT GGC GCA GGA ACC ATT CTG AGA GTC AAG          46
  Gly Asn Lys Leu Val Phe Gly Ala Gly Thr Ile Leu Arg Val Lys
  1               5                   10                  15

TCC T                                                                  50
Ser (2) INFORMATION FOR SEQ ID NO: 21:

(i) SEQUENCE CHARACTERISTICS:
              (A) LENGTH: 22
              (B) TYPE: NUCLEOTIDE
              (C) STRANDEDNESS: SINGLE
              (D) TOPOLOGY: LINEAR (ii) MOLECULE TYPE: OLIGONUCLEOTIDE (ix) FEATURE:
              (A) NAME/KEY:
              (B) LOCATION:
              (C) IDENTIFICATION METHOD:
              (D) OTHER INFORMATION: A
```

(xi) SEQUENCE DESCRIPTION: SEQ ID NO:21:

GTTGCTCCAG GCCACAGCAC TG        22

(2) INFORMATION FOR SEQ ID NO: 22:

(i) SEQUENCE CHARACTERISTICS:
        (A) LENGTH: 35
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: POLY C (xi) SEQUENCE DESCRIPTION: SEQ ID NO:22:

GCATGCGCGC GGCCGCGGAG GCCCCCCCCC CCCCC        35

(2) INFORMATION FOR SEQ ID NO: 23:

(i) SEQUENCE CHARACTERISTICS:
        (A) LENGTH: 26
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: B (xi) SEQUENCE DESCRIPTION: SEQ ID NO:23:

GTCCATAGAC CTCATGTCCA GCACAG        26

(2) INFORMATION FOR SEQ ID NO: 24:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: C (xi) SEQUENCE DESCRIPTION: SEQ ID NO:24:

ATACACATCA GAATTCTTAC TTTG        24

(2) INFORMATION FOR SEQ ID NO: 25:

(i) SEQUENCE CHARACTERISTICS:
        (A) LENGTH: 19
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:

(A) NAME/KEY:
                (B) LOCATION:
                (C) IDENTIFICATION METHOD:
                (D) OTHER INFORMATION:  D (xi) SEQUENCE DESCRIPTION: SEQ ID NO:25:

GTCACTGGAT TTAGAGTCT                                                    19

(2) INFORMATION FOR SEQ ID NO: 26:

(i) SEQUENCE CHARACTERISTICS:
                (A) LENGTH: 24
                (B) TYPE: NUCLEOTIDE
                (C) STRANDEDNESS:  SINGLE
                (D) TOPOLOGY:  LINEAR (ii) MOLECULE TYPE:  OLIGONUCLEOTIDE (ix) FEATURE:
                (A) NAME/KEY:
                (B) LOCATION:
                (C) IDENTIFICATION METHOD:
                (D) OTHER INFORMATION:  TYPE V Alpha 1, CLONE AB22, POSITION
                    235, THE 6TH AND 23RD NUCLEOTIDES CORRESPOND
                    TO MISMATCHES INTRODUCED RELATIVE TO THE NATURAL
                    SEQUENCE (xi) SEQUENCE DESCRIPTION: SEQ ID NO:26:

GGCATTAACG GTTTTGAGGC TGGA                                              24

(2) INFORMATION FOR SEQ ID NO: 27:

(i) SEQUENCE CHARACTERISTICS:
                (A) LENGTH: 24
                (B) TYPE: NUCLEOTIDE
                (C) STRANDEDNESS:  SINGLE
                (D) TOPOLOGY:  LINEAR (ii) MOLECULE TYPE:  OLIGONUCLEOTIDE (ix) FEATURE:
                (A) NAME/KEY:
                (B) LOCATION:
                (C) IDENTIFICATION METHOD:
                (D) OTHER INFORMATION:  TYPE V Alpha 2, CLONE IGRa09,
                    POSITION 93*, THE 24TH NUCLEOTIDE CORRESPONDS TO
                    A MISMATCH INTRODUCED RELATIVE TO THE
                    NATURAL SEQUENCE (xi) SEQUENCE DESCRIPTION: SEQ ID NO:27:

CAGTGTTCCA GAGGGAGCCA TTGC                                              24

(2) INFORMATION FOR SEQ ID NO: 28:

(i) SEQUENCE CHARACTERISTICS:
                (A) LENGTH: 24
                (B) TYPE: NUCLEOTIDE
                (C) STRANDEDNESS:  SINGLE
                (D) TOPOLOGY:  LINEAR (ii) MOLECULE TYPE:  OLIGONUCLEOTIDE (ix) FEATURE:
                (A) NAME/KEY:
                (B) LOCATION:
                (C) IDENTIFICATION METHOD:
                (D) OTHER INFORMATION:  TYPE V Alpha 3, CLONE HAP05, POSITION
                    297

(xi) SEQUENCE DESCRIPTION: SEQ ID NO:28:

CCGGGCAGCA GACACTGCTT CTTA                                              24

(2) INFORMATION FOR SEQ ID NO: 29:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE V Alpha 4, CLONE HAP08, POSITION
            153

(xi) SEQUENCE DESCRIPTION: SEQ ID NO:29:

TTGGTATCGA CAGCTTCCCT CCCA                                            24

(2) INFORMATION FOR SEQ ID NO: 30:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE V Alpha 5, CLONE IGRa10,
            POSITION 113

(xi) SEQUENCE DESCRIPTION: SEQ ID NO:30:

CGGCCACCCT GACCTGCAAC TATA                                            24

(2) INFORMATION FOR SEQ ID NO: 31:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE V Alpha 6, CLONE HAP01, POSITION
            287

(xi) SEQUENCE DESCRIPTION: SEQ ID NO:31:

TCCGCCAACC TTGTCATCTC CGCT                                            24

(2) INFORMATION FOR SEQ ID NO: 32:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:

(D) OTHER INFORMATION: TYPE V Alpha 7, CLONE IGRa11,
POSITION 159, THE 9TH AND 15TH NUCLEOTIDES
CORRESPOND TO MISMATCHES INTRODUCED RELATIVE TO THE
NATURAL SEQUENCE (xi) SEQUENCE DESCRIPTION: SEQ ID NO:32:

GCAACATGCT GGCGGAGCAC CCAC                                            24

(2) INFORMATION FOR SEQ ID NO: 33:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE V Alpha 8, CLONE HAP41, POSITION
            204

(xi) SEQUENCE DESCRIPTION: SEQ ID NO:33:

CATTCGTTCA AATGTGGGCA AAAG                                           24

(2) INFORMATION FOR SEQ ID NO: 34:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE V Alpha 9, CLONE HAVP36,
            POSITION 168, THE 22ND NUCLEOTIDE CORRESPONDS TO A
            MISMATCH INTRODUCED RELATIVE TO THE NATURAL SEQUENCE (xi) SEQUENCE DESCRIPTION: SEQ ID NO:34:

CCAGTACTCC AGACAACGCC TGCA                                           24

(2) INFORMATION FOR SEQ ID NO: 35:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE V Alpha 10, CLONE HAP58,
            POSITION 282

(xi) SEQUENCE DESCRIPTION: SEQ ID NO:35:

CACTGCGGCC CAGCCTGGTG ATAC                                           24

(2) INFORMATION FOR SEQ ID NO: 36:

(i) SEQUENCE CHARACTERISTICS:

```
          (A) LENGTH: 24
          (B) TYPE:  NUCLEOTIDE
          (C) STRANDEDNESS:  SINGLE
          (D) TOPOLOGY:  LINEAR (ii) MOLECULE TYPE:  OLIGONUCLEOTIDE (ix) FEATURE:
          (A) NAME/KEY:
          (B) LOCATION:
          (C) IDENTIFICATION METHOD:
          (D) OTHER INFORMATION:  TYPE V Alpha 11, CLONE AB19, POSITION
              254*

(xi) SEQUENCE DESCRIPTION: SEQ ID NO:36:

CGCTGCTCAT CCTCCAGGTG CGGG                                               24

(2) INFORMATION FOR SEQ ID NO: 37:

(i) SEQUENCE CHARACTERISTICS:
          (A) LENGTH: 24
          (B) TYPE:  NUCLEOTIDE
          (C) STRANDEDNESS:  SINGLE
          (D) TOPOLOGY:  LINEAR (ii) MOLECULE TYPE:  OLIGONUCLEOTIDE (ix) FEATURE:
          (A) NAME/KEY:
          (B) LOCATION:
          (C) IDENTIFICATION METHOD:
          (D) OTHER INFORMATION:  TYPE V Alpha 12, CLONE V12MA483,
              POSITION 213

(xi) SEQUENCE DESCRIPTION: SEQ ID NO:37:

TCGTCGGAAC TCTTTTGATG AGCA                                               24

(2) INFORMATION FOR SEQ ID NO: 38:

(i) SEQUENCE CHARACTERISTICS:
          (A) LENGTH: 24
          (B) TYPE:  NUCLEOTIDE
          (C) STRANDEDNESS:  SINGLE
          (D) TOPOLOGY:  LINEAR (ii) MOLECULE TYPE:  OLIGONUCLEOTIDE (ix) FEATURE:
          (A) NAME/KEY:
          (B) LOCATION:
          (C) IDENTIFICATION METHOD:
          (D) OTHER INFORMATION:  TYPE V Alpha 13, CLONE HAVT15,
              POSITION 152*

(xi) SEQUENCE DESCRIPTION: SEQ ID NO:38:

TTCATCAAAA CCCTTGGGGA CAGC                                               24

(2) INFORMATION FOR SEQ ID NO: 39:

(i) SEQUENCE CHARACTERISTICS:
          (A) LENGTH: 24
          (B) TYPE:  NUCLEOTIDE
          (C) STRANDEDNESS:  SINGLE
          (D) TOPOLOGY:  LINEAR (ii) MOLECULE TYPE:  OLIGONUCLEOTIDE (ix) FEATURE:
          (A) NAME/KEY:
          (B) LOCATION:
          (C) IDENTIFICATION METHOD:
          (D) OTHER INFORMATION:  TYPE V Alpha 14, CLONE HAVT20,
              POSITION 181
```

(xi) SEQUENCE DESCRIPTION: SEQ ID NO:39:

CCCAGCAGGC AGATGATTCT CGTT                                              24

(2) INFORMATION FOR SEQ ID NO: 40:

(i) SEQUENCE CHARACTERISTICS:
        (A) LENGTH: 24
        (B) TYPE:  NUCLEOTIDE
        (C) STRANDEDNESS:  SINGLE
        (D) TOPOLOGY:  LINEAR (ii) MOLECULE TYPE:  OLIGONUCLEOTIDE (ix) FEATURE:
        (A) NAME/KEY:
        (B) LOCATION:
        (C) IDENTIFICATION METHOD:
        (D) OTHER INFORMATION:  TYPE V Alpha 15, CLONE HAVT31,
            POSITION 278, THE 12TH NUCLEOTIDE CORRESPONDS TO A
            MISMATCH INTRODUCED RELATIVE TO THE NATURAL SEQUENCE (xi) SEQUENCE DESCRIPTION: SEQ ID NO:40:

TTGCAGACAC CGAGACTGGG GACT                                              24

(2) INFORMATION FOR SEQ ID NO: 41:

(i) SEQUENCE CHARACTERISTICS:
        (A) LENGTH: 24
        (B) TYPE:  NUCLEOTIDE
        (C) STRANDEDNESS:  SINGLE
        (D) TOPOLOGY:  LINEAR (ii) MOLECULE TYPE:  OLIGONUCLEOTIDE (ix) FEATURE:
        (A) NAME/KEY:
        (B) LOCATION:
        (C) IDENTIFICATION METHOD:
        (D) OTHER INFORMATION:  TYPE V Alpha 16, CLONE IGRa13,
            POSITION 89

(xi) SEQUENCE DESCRIPTION: SEQ ID NO:41:

TCAACGTTGC TGAAGGGAAT CCTC                                              24

(2) INFORMATION FOR SEQ ID NO: 42:

(i) SEQUENCE CHARACTERISTICS:
        (A) LENGTH: 24
        (B) TYPE:  NUCLEOTIDE
        (C) STRANDEDNESS:  SINGLE
        (D) TOPOLOGY:  LINEAR (ii) MOLECULE TYPE:  OLIGONUCLEOTIDE (ix) FEATURE:
        (A) NAME/KEY:
        (B) LOCATION:
        (C) IDENTIFICATION METHOD:
        (D) OTHER INFORMATION:  TYPE V Alpha 17, CLONE AB11,
            POSITION 204, THE 12TH NUCLEOTIDE CORRESPONDS TO
            A MISMATCH INTRODUCED RELATIVE TO THE NATURAL SEQUENCE (xi) SEQUENCE DESCRIPTION: SEQ ID NO:42:

TGGGAAAGGC CGTGCATTAT TGAT                                              24

(2) INFORMATION FOR SEQ ID NO: 43:

(i) SEQUENCE CHARACTERISTICS:
        (A) LENGTH: 24
        (B) TYPE:  NUCLEOTIDE
        (C) STRANDEDNESS:  SINGLE
        (D) TOPOLOGY:  LINEAR (ii) MOLECULE TYPE: OLIGONUCLEOTIDE (ix) FEATURE:
    (A) NAME/KEY:
    (B) LOCATION:
    (C) IDENTIFICATION METHOD:
    (D) OTHER INFORMATION: TYPE V Alpha 18, CLONE AB21, POSITION
        114

(xi) SEQUENCE DESCRIPTION: SEQ ID NO:43:

CAGCACCAAT TTCACCTGCA GCTT                                         24

(2) INFORMATION FOR SEQ ID NO: 44:

(i) SEQUENCE CHARACTERISTICS:
    (A) LENGTH: 24
    (B) TYPE: NUCLEOTIDE
    (C) STRANDEDNESS: SINGLE
    (D) TOPOLOGY: LINEAR (ii) MOLECULE TYPE: OLIGONUCLEOTIDE (ix) FEATURE:
    (A) NAME/KEY:
    (B) LOCATION:
    (C) IDENTIFICATION METHOD:
    (D) OTHER INFORMATION: TYPE V Alpha 19, CLONE AC24, POSITION
        162

(xi) SEQUENCE DESCRIPTION: SEQ ID NO:44:

ACACTGGCTG CAACAGCATC CAGG                                         24

(2) INFORMATION FOR SEQ ID NO: 45:

(i) SEQUENCE CHARACTERISTICS:
    (A) LENGTH: 24
    (B) TYPE: NUCLEOTIDE
    (C) STRANDEDNESS: SINGLE
    (D) TOPOLOGY: LINEAR (ii) MOLECULE TYPE: OLIGONUCLEOTIDE (ix) FEATURE:
    (A) NAME/KEY:
    (B) LOCATION:
    (C) IDENTIFICATION METHOD:
    (D) OTHER INFORMATION: TYPE V Alpha 20, CLONE AE212,
        POSITION 232

(xi) SEQUENCE DESCRIPTION: SEQ ID NO:45:

TCCCTGTTTA TCCCTGCCGA CAGA                                         24

(2) INFORMATION FOR SEQ ID NO: 46:

(i) SEQUENCE CHARACTERISTICS:
    (A) LENGTH: 24
    (B) TYPE: NUCLEOTIDE
    (C) STRANDEDNESS: SINGLE
    (D) TOPOLOGY: LINEAR (ii) MOLECULE TYPE: OLIGONUCLEOTIDE (ix) FEATURE:
    (A) NAME/KEY:
    (B) LOCATION:
    (C) IDENTIFICATION METHOD:
    (D) OTHER INFORMATION: TYPE V Alpha 21, CLONE AF211,
        POSITION 92

(xi) SEQUENCE DESCRIPTION: SEQ ID NO:46:

AGCAAAATTC ACCATCCCTG AGCG                                         24

(2) INFORMATION FOR SEQ ID NO: 47:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE V Alpha 22, CLONE IGRa12,
            POSITION 197

(xi) SEQUENCE DESCRIPTION: SEQ ID NO:47:

CCTGAAAGCC ACGAAGGCTG ATGA                                        24

(2) INFORMATION FOR SEQ ID NO: 48:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE V Alpha w23, CLONE IGRa01,
            POSITION 246

(xi) SEQUENCE DESCRIPTION: SEQ ID NO:48:

TGCCTCGCTG GATAAATCAT CAGG                                        24

(2) INFORMATION FOR SEQ ID NO: 49:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE V Alpha w24, CLONE IGRa02,
            POSITION 259, THE 21ST NUCLEOTIDE CORRESPONDS TO A
            MISMATCH INTRODUCED RELATIVE TO THE NATURAL SEQUENCE (xi) SEQUENCE DESCRIPTION: SEQ ID NO:49:

CTGGATGCAG ACACAAAGCA GAGC                                        24

(2) INFORMATION FOR SEQ ID NO: 50:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:

(B) LOCATION:
            (C) IDENTIFICATION METHOD:
            (D) OTHER INFORMATION: TYPE V Alpha w25, CLONE IGRA03,
                POSITION 148, THE 7TH AND 17TH NUCLEOTIDES
                CORRESPOND TO MISMATCHES INTRODUCED RELATIVE TO THE
                NATURAL SEQUENCE (xi) SEQUENCE DESCRIPTION:SEQ ID NO:50:

TGGCTACGGT ACAAGCCGGA CCCT                                              24

(2) INFORMATION FOR SEQ ID NO: 51:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE V Alpha w26, CLONE IGRa04,
            POSITION 299, THE 4TH AND 20TH NUCLEOTIDES
            CORRESPOND TO MISMATCHES INTRODUCED RELATIVE TO THE
            NATURAL SEQUENCE (xi) SEQUENCE DESCRIPTION: SEQ ID NO:51:

AGCGCAGCCA TGCAGGCATG TACC                                              24

(2) INFORMATION FOR SEQ ID NO: 52:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE V Alpha w27, CLONE IGRa05,
            POSITION 268*

(xi) SEQUENCE DESCRIPTION: SEQ ID NO:52:

AAGCCCGTCT CAGCACCCTC CACA                                              24

(2) INFORMATION FOR SEQ ID NO: 53:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE V Alpha w28, CLONE IGRa06,
            POSITION 95, THE 8TH AND 15TH NUCLEOTIDES
            CORRESPOND TO MISMATCHES INTRODUCED RELATIVE TO THE
            NATURAL SEQUENCE (xi) SEQUENCE DESCRIPTION: SEQ ID NO:53:

TGGTTGTGCA CGAGCGAGAC ACTG                                              24

(2) INFORMATION FOR SEQ ID NO: 54:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE V Alpha w29, CLONE IGRa07,
            POSITION 210

(xi) SEQUENCE DESCRIPTION: SEQ ID NO:54:

GAAGGGTGGA GAACAGATGC GTCG                                      24

(2) INFORMATION FOR SEQ ID NO: 55:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE C Alpha A, POSITION 129

(xi) SEQUENCE DESCRIPTION: SEQ ID NO:55:

ATACACATCA GAATTCTTAC TTTG                                      24

(2) INFORMATION FOR SEQ ID NO: 56:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE C Alpha B, POSITION 201

(xi) SEQUENCE DESCRIPTION: SEQ ID NO:56:

GTTGCTCCAG GCCGCGGCAC TGTT                                      24

(2) INFORMATION FOR SEQ ID NO: 57:

(i) SEQUENCE CHARACTERISTICS:
        (A) LENGTH: 19
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:

(D) OTHER INFORMATION: TYPE C Alpha C, POSITION 57

(xi) SEQUENCE DESCRIPTION: SEQ ID NO:57:

GTCACTGGAT TTAGAGTCT                                                19

(2) INFORMATION FOR SEQ ID NO: 58:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE Act 1, CLONE Beta-actin,
            POSITION 1161

(xi) SEQUENCE DESCRIPTION: SEQ ID NO:58:

ATTTGCGGTG GACGATGGAG GGGC                                          24

(2) INFORMATION FOR SEQ ID NO: 59:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE Act 2, CLONE Beta-ACTIN,
            POSITION 261

(xi) SEQUENCE DESCRIPTION: SEQ ID NO:59:

GGCATCGTCA CCAACTGGGA CGAC                                          24

(2) INFORMATION FOR SEQ ID NO: 60:

(i) SEQUENCE CHARACTERISTICS:
        (A) LENGTH: 19
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE Act 3, CLONE Beta-ACTIN,
            POSITION 642

(xi) SEQUENCE DESCRIPTION: SEQ ID NO:60:

ACCACCACGG CGGAGCGGG                                                19

(2) INFORMATION FOR SEQ ID NO: 61:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE:  OLIGONUCLEOTIDE (ix) FEATURE:
             (A) NAME/KEY:
             (B) LOCATION:
             (C) IDENTIFICATION METHOD:
             (D) OTHER INFORMATION:  TYPE C Beta F, POSITION 135

(xi) SEQUENCE DESCRIPTION: SEQ ID NO:61:

CGGGCTGCTC CTTGAGGGGC TGCG                                                  24

(2) INFORMATION FOR SEQ ID NO: 62:

(i) SEQUENCE CHARACTERISTICS:
            (A) LENGTH: 19
            (B) TYPE:  NUCLEOTIDE
            (C) STRANDEDNESS:  SINGLE
            (D) TOPOLOGY:  LINEAR (ii) MOLECULE TYPE:  OLIGONUCLEOTIDE (ix) FEATURE:
             (A) NAME/KEY:
             (B) LOCATION:
             (C) IDENTIFICATION METHOD:
             (D) OTHER INFORMATION:  TYPE C Beta K, POSITION 20

(xi) SEQUENCE DESCRIPTION: SEQ ID NO:62:

CCCACCCGAG GTCGCTGTG                                                        19

(2) INFORMATION FOR SEQ ID NO: 63:

(i) SEQUENCE CHARACTERISTICS:
            (A) LENGTH: 19
            (B) TYPE:  NUCLEOTIDE
            (C) STRANDEDNESS:  SINGLE
            (D) TOPOLOGY:  LINEAR (ii) MOLECULE TYPE:  OLIGONUCLEOTIDE (ix) FEATURE:
             (A) NAME/KEY:
             (B) LOCATION:
             (C) IDENTIFICATION METHOD:
             (D) OTHER INFORMATION:  TYPE C Beta C, POSITION 58

(xi) SEQUENCE DESCRIPTION: SEQ ID NO:63:

TCTGCTTCTG ATGGCTCAA                                                        19